US008728980B2

United States Patent
Wang et al.

(10) Patent No.: US 8,728,980 B2
(45) Date of Patent: May 20, 2014

(54) PEPTIDE MICROARRAY AND METHOD OF USE

(71) Applicant: The Regents of the University of California, Oakland, CA (US)

(72) Inventors: Wei Wang, La Jolla, CA (US); Zheng Xu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/666,284

(22) Filed: Nov. 1, 2012

(65) Prior Publication Data

US 2013/0116146 A1 May 9, 2013

Related U.S. Application Data

(60) Provisional application No. 61/555,778, filed on Nov. 4, 2011.

(51) Int. Cl.
*C40B 30/04* (2006.01)
*G01N 33/68* (2006.01)

(52) U.S. Cl.
USPC ............................................. 506/9; 435/7.1

(58) Field of Classification Search
USPC ....................................................... 506/9, 18
See application file for complete search history.

(56) References Cited

PUBLICATIONS

Panicker et al., "Recent Advances in Peptide-Based Microarray Technologies," Comb. Chem. High Throughput Screen. 2004, 7:547-556.*
Schutkowski et al., "Peptide Arrays for Kinase Profiling," ChemBioChem 2005, 6:513-521.*
Andresen et al., "Functional peptide microarrays for specific and sensitive antibody diagnostics," Proteomics 2006, 6:1376-1384.*
Altschul, et al., 1990, "Basic local alignment search tool," J Mol Biol, 215, 403-410.
Cheng et al., 2005, "Scratch: a protein structure and structural feature prediction server," Nucleic Acids Res, 33, W72-76.
Craig et al., 2004, "Tandem: matching proteins with tandem mass spectra," Bioinformatics 20, 1466-1467.
Deutsch et al., 2008, "PeptideAtlas: a resource for target selection for emerging targeted proteomics workflows," EMBO Rep, 9, 429-434.
Geer et al., 2004, "Open mass spectrometry search algorithm," J. Proteome Res. 3, 958-964.
Hou et al., 2006, "Computational analysis and prediction of the binding motif and protein interacting partners of the Abl SH3 domain," PLoS Comput Biol 2, el.
Hou et al., 2008, "Characterization of domain-peptide interaction interface: a case study on the amphiphysin-1 SH3 domain," J Mol Biol 376, 1201-1214.

(Continued)

*Primary Examiner* — Samuel Woolwine
*Assistant Examiner* — Kaijiang Zhang
(74) *Attorney, Agent, or Firm* — Sutherland Asbill & Brennan LLP

(57) ABSTRACT

A peptide microarray comprising a plurality of predicted unique binding peptides being selected by computational prediction of interaction with a protein of interest or a domain thereof. The selected unique binding peptides are pre-synthesized and then printed and/or immobilized onto a solid support surface via N-terminus with a linker. Methods of using the invention peptide microarray for quantitative determination of protein-peptide interaction, epitope mapping, and drug screening are also provided.

11 Claims, 8 Drawing Sheets

(56) References Cited

PUBLICATIONS

Hou et al., 2009, "Characterization of domain-peptide interaction interface: a generic structure-based model to decipher the binding specificity of SH3 domains," Mol Cell Proteomics 8, 639-649.

Hou et al., 2011, "Prediction of peptides binding to the PKA RIIalpha subunit using a hierarchical strategy," Bioinformatics 27(13): 1814-1821.

Hou et al., 2012, "Characterization of Domain-Peptide Interaction Interface: Prediction of SH3 Domain-Mediated Protein-Protein Interaction Network in Yeast by Generic Structure-Based Models," J. Proteome Res.11(5): 2982-2995.

Jain et al., 2009, "Infrastructure for the life sciences: design and implementation of the UniProt website," BMC Bioinformatics, 10, 136.

Jones, 1999, "Protein secondary structure prediction based on position-specific scoring matrices," J Mol Biol, 292, 195-202.

Kabsch et al., 1983, "Dictionary of protein secondary structure: pattern recognition of hydrogen-bonded and geometrical features," Biopolymers, 22, 2577-2637.

Kollman et al., 2000, "Calculating structures and free energies of complex molecules: combining molecular mechanics and continuum models," Accounts of Chemical Research 33, 889-897.

Larkin et al., 2007, "Clustal W and Clustal X version 2.0," Bioinformatics, 23, 2947-2948.

Tanner et al., 2005, "InsPecT: identification of post-translationally modified peptides from tandem mass spectra," Anal. Chem. 77, 4626-4639.

The UniProt Consortium, 2010, "The Universal Protein Resource (UniProt) in 2010," Nucleic Acids Res, 38, D142-148.

Vizcaino et al., 2009, "A guide to the Proteomics Identifications Database proteomics data repository," Proteomics 9, 4276-4283.

Wang et al., 2001, "Biomolecular simulations: recent developments in force fields, simulations of enzyme catalysis, protein-ligand, protein-protein, and protein-nucleic acid noncovalent interactions," Annu. Rev. Biophys. Biomol. Struct. 30, 211-243.

Wu et al., 2007, "Systematic identification of SH3 domain-mediated human protein-protein interactions by peptide array target screening," Proteomics 7, 1775-1785.

Xu et al., 2012, "Proteome-wide detection of Abl1 SH3-binding peptides by integrating computational prediction and peptide microarray," Mol. Cell Proteomics 11(1): O111 010389.

Zhang et al., 2004, "Some basic data structures and algorithms for chemical generic programming," Journal of Chemical Information and Computer Sciences 44, 1571-1575.

* cited by examiner

PEPTIDE MICROARRAY AND METHOD OF USE

CROSS REFERENCES TO RELATED APPLICATIONS

This application claims priority from U.S. Provisional Application Ser. No. 61/555,778 filed on Nov. 4, 2011, which is incorporated herein by reference in its entirety.

STATEMENT OF GOVERNMENT INTEREST

This invention was made with government support under grant No. GM085188 awarded by National Institutes of Health (NIH). The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 22, 2012, is named 24978019.txt and is 23,255 bytes in size.

FIELD OF THE INVENTION

This invention relates to peptide microarrays and methods of use thereof, for identifying protein-protein interactions.

BACKGROUND OF THE INVENTION

A peptide microarray (also commonly known as peptide chip or peptide epitope microarray) is a collection of peptides displayed on a solid surface, usually a glass or plastic chip. Peptide chips are used by scientists in biology, medicine and pharmacology to study binding properties and functionality and kinetics of protein-protein interactions in general. In basic research, peptide microarrays are often used to profile an enzyme (like kinase, phosphatase, protease, acetyltransferase, histone deacetylase, etc.), to map an antibody epitope or to find key residues for protein binding. Practical applications include seromarker discovery, profiling of changing humoral immune responses of individual patients during disease progression, monitoring of therapeutic interventions, patient stratification and development of diagnostic tools and vaccines.

The assay principle of peptide microarrays is similar to an ELISA protocol. The peptides (thousands in several copies) are linked to the surface of a glass chip. This peptide chip can directly be incubated with a variety of different biological samples, such as purified enzymes or antibodies, patient or animal sera, cell lysates, etc. After several washing steps, a secondary antibody with the needed specificity (e.g., anti IgG human/mouse or anti phosphotyrosine or anti myc) is applied. Typically, the secondary antibody is tagged by a fluorescence label that can be detected by a fluorescence scanner. Other detection methods include chemiluminescence or autoradiography.

Therefore, a peptide microarray is a planar slide with peptides spotted onto it or assembled directly on the surface. Whereas spotting peptides with current techniques can undergo quality control prior to spotting and result from a single synthetic batch, peptides synthesized directly on the surface may suffer from batch-to-batch variation and limited quality control options. However, spotting peptides onto a support surface still has current significant limitations. One limitation is the large size of the peptide array required, which restricts its capability to be scaled up for proteomic measurements. A second limitation is that the peptide spotting output is often qualitative rather than quantitative. A third limitation is the high cost of peptide synthesis and limited access to the necessary instruments, which has prohibited its implementation as a routine technology. Other limitations exist in the current technology.

Therefore, there is a need to develop a peptide microarray technology that improves upon the prior art.

SUMMARY OF THE INVENTION

The invention provides a peptide microarray comprising a solid support surface and a plurality of predicted unique binding peptides being pre-synthesized and immobilized onto the solid support surface by a linker, wherein the predicted unique binding peptides have been selected for the microarray by computational prediction of interaction with a protein of interest or a domain thereof. In certain embodiments, the peptide microarray of the present invention contains between 10-10,000, 50-5,000, 100-1,000, 200-900, 300-800, or 400-700, including any number in between of predicted unique binding peptides or domains thereof immobilized on the solid support surface. In certain embodiments, the protein of interest or a domain thereof or the predicted binding peptides are modified including, but not limited to, methylation or acetylation. In certain embodiments, multiple copies of each predicted unique binding peptide are immobilized on the solid support.

In certain embodiments, the linker attached to the predicted binding peptides for peptide immobilization on the solid support surface of the microarray includes, but is not limited to aminohexanoic acid (Ahx) or polyethylene glycol (PEG). In certain embodiments, the predicted binding peptides are capped with Alanine at each terminus. Any suitable linkers or capping molecules, now known or later developed in the art, that are used in any type of microarray technologies are encompassed in the present invention.

The present invention provides that the predicted unique binding peptides are selected for microarray by computational prediction. In certain embodiments, the computational prediction comprises a combination of at least three analytical approaches selected from the group consisting of structural information, energetic pattern of said peptide-protein interactions, e.g. van der Waals, electrostatic and desolvation energies, molecular dynamics simulation, conservation during evolution, mutation, subcellular location, functional filtering processes, proteome scan, and mass spectra evidence. In certain embodiments, the computational prediction comprises a combination of at least four, five, six, seven, eight, nine, ten, or more structural and/or functional computational approaches, now known or later developed in the art, for selecting predicted binding peptides.

The present invention further provides a method of identifying one or more binding peptides interacting with a protein of interest or a domain thereof, comprising the steps of a) providing computational prediction for binding peptides to the protein of interest or a domain thereof; b) selecting a plurality of the predicted unique binding peptides based on the computational prediction; c) generating a peptide microarray comprising the plurality of predicted unique binding peptides being pre-synthesized and immobilized on a solid support surface by a linker; d) exposing the microarray to the protein of interest or domain thereof; and e) detecting interactions of one or more predicted unique binding peptide with the protein of interest or domain thereof on the microarray, thereby identifying one or more binding peptides interacting with a protein of interest or a domain thereof.

In certain embodiments, the inventive method is capable of identifying a binding peptide-protein interaction when the binding peptide and/or the protein of interest or a domain thereof are either unmodified or modified including, but not limited to methylation or acetylation. The present invention, thus, provides a use of the peptide microarray in combination with computational prediction for identifying unmodified and/or modified binding peptides, proteins of interest, or a domain or motif thereof. In certain embodiments, the modified binding peptides, proteins of interest, or a domain or motif thereof, include post-translational modification (PTM) proteins that regulate lysine methylation.

In other embodiments, the inventive method is also capable of identifying and/or detecting and quantitating transient interaction between a binding peptide and the protein of interest or a domain thereof. In certain embodiments, the interaction between the binding peptides and the protein of interest or a domain thereof is detected via a fluorescent signal that correlates with a binding affinity and provides a quantitative measurement of interaction between the binding peptides and protein of interest or a domain thereof. Any other detection methods, now known or later developed in the art, that are used in any type of microarray technologies are also encompassed in the present invention. Use of the peptide microarray of the present invention for epitope mapping and drug screening or vaccine development, as non-limiting examples, is also provided.

BRIEF DESCRIPTION OF THE DRAWINGS

FIG. 2 discloses SEQ ID NOS 107-126, respectively, in order of appearance.

FIG. 7 discloses "Asp23 to Glu29" as SEQ ID NO: 127.

FIG. 10 discloses "L20 to R26" as SEQ ID NO: 130.

DETAILED DESCRIPTION OF THE INVENTION

Figure 1:
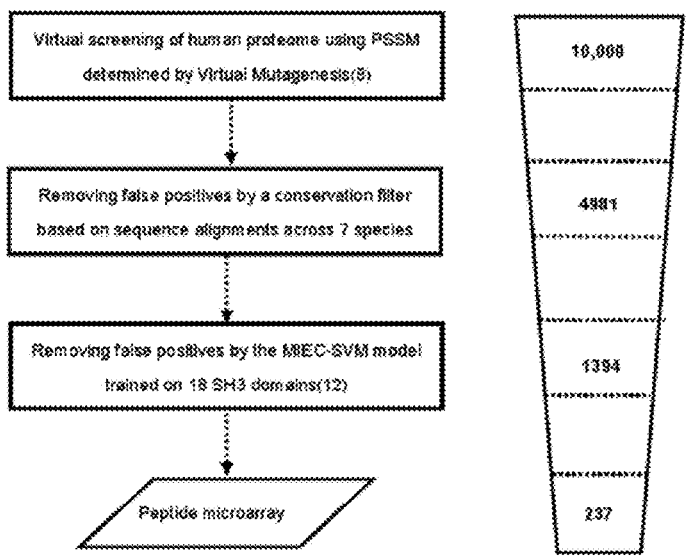
FIG. 1 illustrates an exemplary flow chart of computational predictive analysis for identifying potential binding peptides of the Abl1 SH3 domain in the human proteome. The numbers on the right indicate the numbers of peptides remained after the step on the left. (1) 69,404 peptides containing the PxxP motif in the human proteome were started with. All the peptides were ranked by the PSSM determined in reference (8). This PSSM was generated by mutating the peptide residue at each position to all other 19 amino acids. Binding free energy difference between the wild type and mutated peptides was calculated to represent the preference of amino acids at a specific peptide position. Top 10,000 peptides ranked by the PSSM were selected for further analysis. (2) Because the Abl1 SH3 domain is completely conserved in 7 species, the binding peptides are likely to be conserved as well. A conservation filter was applied to identify the most reliable interacting partners of Abl1 and 4,981 peptides passed this filter. (3) A classification model called MIEC-SVM was sequentially applied to remove false positives. This MIEC-SVM model was based on energetic characterization of the SH3-peptide interaction interface and was trained on 18 SH3 domains in a previous study (12). The MIEC-SVM model predicted 1,394 peptides as binders. (4) The top 700 in the 1394 peptides (ranked by the PSSM) were synthesized and printed/immobilized on a microarray. 237 peptides showed significant binding intensity and were considered as potential binding partners of the Abl1 SH3 domain.

The invention provides a peptide microarray comprising a solid support surface onto which a plurality of predicted unique binding peptides is immobilized by a linker. The predicted unique binding peptides have been previously selected for the microarray by computational prediction of interaction with a protein of interest or a domain thereof. After the computational prediction selection, the predicted unique binding peptides are synthesized before being immobilized onto the solid support surface of the microarray. Any suitable solid support surface, now known or later developed, that can be used in any types of microarray technologies, are encompassed in the present invention. In certain embodiments, the solid support surface of the peptide microarray is a glass surface. As used herein, the terms "microarray" and/or "peptide microarray" (or "peptide chip") are well known in the art, and refer to a collection of peptide displayed on a solid surface, usually a glass or plastic chip, and being used to study binding properties and functionality and kinetics of protein-protein interactions in general.

The peptide microarray of the present invention with the predicted unique binding peptides pre-synthesized and then printed on a glass surface significantly reduces the size of the array. The peptide microarray of the present invention requires much fewer peptides than a traditional peptide microarray due to the computational prediction analysis. Using the peptide microarray of the present invention, very little protein is also required for analysis, which is particularly useful in disease diagnosis where the amount of patient sample is usually limited. The inventive peptide microarray, and method of use thereof, significantly reduces the cost of generating and applying the peptide microarray.

In certain embodiments, the peptide microarray of the present invention contains 10-10,000, 50-5,000, 100-1,000, 200-900, 300-800, or 400-700, including any number in between of predicted unique binding peptides or domains thereof immobilized on the solid support surface. In certain embodiments, the microarray contains less than 1,000 unique predicted binding peptides. In certain embodiments, the predicted unique binding peptides or domains thereof are modified including, but not limited to, methylation or acetylation. As used herein, the terms "peptide" and/or "protein" are used interchangeable, usually refer to a chain of short polymers of amino acid monomers linked by peptide bonds, which are the covalent chemical bonds formed between two molecules when the carboxyl group of one molecule reacts with the amino group of the other molecule. The term "peptide" usually refers to a shorter chain typically containing fewer than 50 monomer units, whereas "protein" usually refers to a longer chain typically containing over hundreds of amino acid monomers.

As used herein, a "peptide" or "polypeptide" includes a compound of two or more subunit amino acids, amino acid analogs, or peptidomimetics. The subunits maybe linked by peptide bonds. In another embodiment, the subunit may be linked by other bonds, e.g., ester, ether, etc. As used herein, the term "amino acid" includes either natural and/or unnatural or synthetic amino acids, including both the D or L optical isomers, and amino acid analogs and peptidomimetics. A "protein" referred to herein is generally 50 amino acids in length or greater. The peptides of the present invention can vary in length from more than 2 and less than 50 amino acids, or between 3-30, 4-20, 5-15, or 6, 7, 8, 9, 10, 11 or 12 amino acids.

As used herein, the proteins and/or binding peptides may comprise modified amino acids, including, but not limited to, methylated or acetylated amino acids and/or amino acid analogs. If present, modifications to the amino acid structure may be imparted before or after assembly of the polymer. The sequence of amino acids may be interrupted by non-amino acid components. A peptide chain may be further modified after polymerization, such as by conjugation with a labeling component, a linker, and/or a capping molecule on either or both C- and N-terminus. Proteins and/or binding peptides of the present invention may be naturally-occurring, synthetic, recombinant, chimeric, or any combination thereof. The present invention encompass proteins and/or binding peptides from any species or resources, including but not limited to, human, mammal, animal, plant, bacteria, fungus, virus, etc. Methods of isolating and purification of a protein or peptide, as well as methods of synthesizing or making a recombinant and/or chimeric protein, are well known in the art.

As used herein, the terms "domain" or "motif" can be used interchangeably, and refer to a structural or functional fragment or part of a given protein sequence and structure that may evolve, function, and exist independently of the rest of the protein chain. The length of the "domain" or "motif" or "fragment" can vary and is usually between about 25 amino acids up to 500 amino acids in length.

Before immobilized onto a solid support surface in the present microarray, the predicted unique binding peptides are synthesized in situ and then attached to a linker for stabilizing the immobilization. In certain embodiments, the linker attached to the predicted binding peptides includes, but is not limited to, aminohexanoic acid (Ahx) or polyethylene glycol (PEG). In certain embodiments, each terminus of the predicted binding peptides is also capped with Alanine. The present invention encompass any suitable linkers or capping molecules, now known or later developed in the art, that can be used in any type of microarray technologies.

Various publications, including patents, published applications, technical articles and scholarly journals are cited throughout the specification. Each of these cited publications is incorporated by reference herein, in its entirety.

The present invention provides that the predicted unique binding peptides are selected for microarray by computational prediction as discussed, for instance, by Hou et al. (*PLoSComput. Biol.*: 0046-005, 2006 & *Mol. Cell Proteomics* 8: 639-649, 2009), the entire contents of each is incorporated by reference herewith. As used herein, the term "computational prediction" refers to any methods and/or analytical approaches utilizing a central processing unit of a computer capable of determining primary, secondary, and tertiary protein structures and functions, and protein-protein interactions. In certain embodiments, the computational prediction comprises a combination of at least three analytical approaches selected from the group consisting of structural information, energetic pattern of said peptide-protein interactions, e.g. van der Waals, electrostatic and desolvation energies, molecular dynamics simulation, conservation during evolution, mutation, subcellular location, functional filtering processes, proteome scan, and mass spectra evidence. In certain embodiments, the computational prediction comprises a combination of at least four or more structural and/or functional approaches, now known or later developed in the art, for selecting predicted binding peptides. For example, mass spectra data can be downloaded from databases of PRIDE (Vizcaino et al., A guide to the Proteomics Identifications Database proteomics data repository. *Proteomics* 2009, 9, 4276-4283) and peptideAtla (Deutsch et al., PeptideAtlas: a resource for target selection for emerging targeted proteomics workflows. *EMBO Rep* 2008, 9, 429-434) and analysis can be performed using software X!TANDEM (Craig and Beavis, TANDEM: matching proteins with tandem mass spectra. *Bioinformatics* 2004, 20, 1466-1467) and INSPECT (Tanner et al., InsPecT: identification of posttranslationally modified peptides from tandem mass spectra. *Anal Chem* 2005, 77, 4626-4639) secondary structures can be predicted by PSI-PRED3.0 (Jones, Protein secondary structure prediction based on position-specific scoring matrices. *J Mol Biol* 1999, 292, 195-202) and SSpro4.0 (Chenget al., SCRATCH: a protein structure and structural feature prediction server. *Nucleic Acids Res* 2005, 33, W72-76); solvent accessible surface area (SASA) can be calculated using DSSP (Kabsch & Sander, Dictionary of protein secondary structure: pattern recognition of hydrogen-bonded and geometrical features. *Biopolymers*

1983, 22, 2577-2637); multiple sequence alignment and conservation can be evaluated by BLAST (Altschul, et al., Basic local alignment search tool. *J Mol Biol* 1990, 215, 403-410) and CLUSTALW2 (Larkin et al., Clustal W and Clustal X version 2.0. *Bioinformatics* 2007, 23, 2947-2948).

The present invention further provides a method of identifying one or more binding peptides interacting with a protein of interest or a domain thereof, comprising the steps of a) providing computational prediction for binding peptides to the protein of interest or a domain thereof; b) selecting a plurality of the predicted unique binding peptides based on the computational prediction; c) generating a peptide microarray comprising the plurality of predicted unique binding peptides being pre-synthesized and immobilized on a solid support surface by a linker; d) exposing the microarray to the protein of interest or domain thereof; and e) detecting interactions of one or more predicted unique binding peptide with the protein of interest or domain thereof on the microarray, thereby identifying one or more binding peptides interacting with a protein of interest or a domain thereof.

In one aspect, the present invention provides a peptide microarray technology that involves chemically synthesizing peptides and printing peptides on a DNA microarray-sized glass slide. The slide is incubated with the protein of interest, followed by a primary antibody recognizing the protein and then a fluorescently-labeled secondary antibody. The slide is scanned with a standard DNA-microarray scanner and the fluorescent intensity of each peptide spot is measured. Binding of the protein to a peptide generates a fluorescent signal and the signal intensity correlates with their binding affinity, which provides a quantitative measurement of protein-peptide interaction. In other embodiments, the inventive method is also capable of identifying and/or detecting transient interaction between a binding peptide and the protein of interest or a domain thereof. Any other detection methods, now known or later developed in the art, that are used in any type of microarray technologies are also encompassed in the present invention.

In one embodiment, the present invention provides a recombinant protein, such as the SH3 domain of c-Abl fused to GST, and a set of testing peptides. The known peptide binder of this SH3 domain displays a fluorescent signal, whereas random peptides as well as peptide binders of other SH3 domains had no signal. The optimization of the peptide microarray printing technology and assay conditions, as well as a determination of whether the intensity of the fluorescent signal and the protein-peptide binding affinity shows a linear correlation, are further provided in Example 1.

In further embodiments, the present invention provides a systematic approach that integrates computer modeling and a peptide microarray technology to identify binding peptides of the SH3 domain of the tyrosine kinase Abl1 in the human proteome. The invention provides a comprehensive list of candidate interacting partners for the Abl1 protein, among which the presence of numerous methyltransferases and RNA slicing proteins may suggest a novel function of Abl1 in chromatin remodeling and RNA processing. This embodiment of the invention illustrates a powerful approach of integrating computational and experimental methods of using the peptide microarray technology to detect protein interactions mediated by domain-peptide recognition.

The present invention further provides that in combination with the computational prediction, the peptide microarray and the inventive method can be used for identifying a binding peptide-protein interaction when the binding peptide and/or the protein of interest or a domain or motif thereof are either unmodified or modified including, but not limited to methylation or acetylation. In certain embodiments, the modified binding peptides, protein of interest, or a domain or motif thereof, are methylated or acetylated peptides or proteins including, but not limited to, post-translational modification (PTM) proteins that regulate lysine methylation.

In one aspect, the present invention provides a systematic approach that integrates computational prediction including bioinformatics pipeline evidence, such as conservation, sub-cellular localization and mass spectrometry data, and a peptide microarray to recognize methylated peptides by Polycomb Chromodomain protein, and to identify methyllysine-containing peptides from the fly proteome. More detailed discussions of these embodiments are provided below in Example 2.

Thus, the present invention provides a peptide microarray technology that can quantitatively determine the binding affinities of peptides on the microarray to the protein of interest, and thus, provides a quantitative, high-throughput, and cost-effective way to conduct proteomics measurements. By printing different sets of peptides on a microarray, the peptide microarray technology of the present invention can be used for defining protein binding specificity, illustrating protein-protein interactions, determining epitopes recognized by antibodies, and identifying substrates of various enzymes. The commercial applications for the invention peptide microarray technology also include, but are not limited to: 1) research use to simultaneously study the interaction of protein(s) of interest with thousands of peptides in a quantitative manner, and 2) epitope mapping for disease diagnosis (e.g. autoimmune diseases and allergies) and drug screening (e.g. vaccine development).

The invention is further illustrated by the following examples, which are not to be construed in any way as imposing limitations upon the scope thereof. It is apparent for skill artisans that various modifications and changes are possible and are contemplated within the scope of the current invention.

EXAMPLES

Example 1

Proteome-wide Detection of Abl1 SH3 Binding Peptides by Integrating Computational Prediction and Peptide Microarray Introduction The human tyrosine kinase Abl1 plays important roles in signal transduction and interacts with a broad variety of cellular proteins (1, 2). Fusion of the break-point cluster region (BCR) and ABL genes form the oncogenic BCR-ABL, which is causally linked to certain human leukemias (3). The Abl1 protein consists of several modular domains, including one SH3 and one SH2 domain that form intra- and inter-molecular interactions to regulate its kinase activity (1, 2). Although many interacting partners of Abl1, such as Abi1, Abi2 and Rin1, have been reported (2), a proteome-wide identification of those mediated by the weak and transient SH3-peptide interaction is still incomplete and remains a challenging problem.

High throughput technologies such as yeast two-hybrid and protein complex purification in conjunction with mass spectrometry have greatly facilitated the identification of protein-protein interactions. However, because they are not optimally designed to detect the weak and transient domain-peptide interactions, such interactions are often underrepresented in proteomic screenings (4, 5). On the other hand, in vitro binding assays such as phage display, peptide array and protein array are often employed to determine the binding specificity of modular domains. Each of these technologies has advantages and limitations. Phage display and peptide array are complementary techniques: the former can test binding of a huge number of random peptides against a given domain while the later can determine binding of a set of specific peptides of interest. Compared with these two techniques, protein array often presents a relatively smaller number of proteins on a surface to test binding of synthesized peptides or purified proteins. Computational analysis is critical to these in vivo or in vitro experimental measurements as it 1) removes false positives and recovering false negatives for the in vivo data; 2) predicts proteome-wide interacting partners based on binding motifs determined by in vitro experiments to guide further experimental investigation.

An integrative approach was presented herewith to identify interacting partners of Abl1 in the human proteome: computational predictions were made by combining multiple sources of data, including structural information, energetic pattern of SH3-peptide interactions and conservation during evolution; the predicted interactions were then tested using a peptide microarray technology. Different from the popular SPOT technology that synthesizes peptides on a cellulose membrane (6), pre-synthesized and quality-controlled peptides were printed and immobilized on a glass surface to hybridize with the purified Abl1 SH3 domain, which confirmed 237 predicted interactions. Proteome-wide identification of putative interacting partners of Abl1 mediated by the SH3-peptide interactions reveals novel functions of Abl1 in chromatin remodeling and RNA processing. It also greatly enhances an understanding of the regulatory mechanism of Abl1.

Methods

I. Computational Prediction of Abl SH3 Binding Peptides

1. Database Screening Using a Position Specific Scoring Matrix (PSSM) Derived from Free Energy Calculations All ten-residue long peptides in the UniProt database (7) were scored using the PSSM we developed in a previous study (8). The PSSM was a 10×20 matrix, which represented the difference in binding free energies between the mutated peptides and the template peptide (see details in (8)). Briefly, the binding free energy of the template peptide was calculated based on the crystal structure (PDB entry 1bbz) using MM/PBSA. Each residue in the peptide to every amino acid of the other 19 was then mutated and the change in binding free energy was calculated. This change reflected the preference of an amino acid at each peptide residue and was encoded in a 10×20 matrix to use as a PSSM to score peptide sequences. The peptide score was computed as:

$$\sum_{i=1}^{10} M_{s,i} \delta(S, S_i),$$

where $M_{s,i}$ was the score of the amino acid S at $i^{th}$ position in the PSSM and $S_i$ was the amino acid at the $i^{th}$ position of the peptide. The top 10,000 peptides with a PxxP motif (x represents any amino acid) were saved for further analyses.

2. Conservation Analysis Across Seven Species

The conservation analysis was conducted on seven species: *Homo sapiens* (human), *Pan troglodytes* (chimpanzee), *Macaca mulatta* (rhesus macaque), *Mus musculus* (mouse), *Rattus norvegicus* (rat), *Canis familiaris* (dog) and *Bos taurus* (cow). The protein sequences of the seven species were taken from the non-redundant protein sequence database at the NCBI BLAST server. For each protein containing the putative binding peptide, the best match found by PSI-BLAST (33) in each species was considered as a homologue if its E-value $<10^{-10}$; otherwise, no homologue. The human protein and its homologues were then aligned using ClustalW 1.7(34). Next, for the 10-residue long putative binding peptide, a pair-wise similarity score:

$$\sum_{i=1}^{10} S_{AiBi} / \sum_{i=1}^{10} S_{AiA}i,$$

where $S_{AiBi}$ was the amino acid similarity score in the PAM500 mutation matrix between residue A at the ith position in the human peptide and residue B at the ith position in the other species was calculated. If a gap was found in the corresponding peptide in any species, this peptide was not considered as a homologue. If no homologue was found, the conservation analysis was not informative and the sequence similarity was set to 1.0. The peptide was conserved only if the pair-wise similarity was equal to or larger than 0.9. In addition, a human peptide was included in the list only if it was conserved in at least four other species.

3. Distinguishing Binders and Non-binders Using the MIEC-SVM Model

Considering the noise in free energy calculation that might affect the accuracy of the PSSM, the MIEC-SVM model developed in the previous study (12) was used to classify all conserved peptides into binder and non-binder groups.

(1) Modeling the complexes for all conserved peptides. The crystal structure of the peptide APSYSPPPPP (SEQ ID NO: 1) in complex with the Abl SH3 domain (PDB entry 1bbz) was used as the initial template to model complexes containing the other peptides. The peptide in the template was systematically mutated to another peptide using the scap program (35). Because of the large number of peptides under consideration, only each modeled structure was minimized using the sander program in AMBER9.0 (36) and the AMBER03 force field (37). The solvent effect was taken into account using the generalized Born (GB) model (igb=2) implemented in sander (38). The maximum number of minimization steps was set to 4,000 and the convergence criterion for the root-mean-square (rms) of the Cartesian elements of the energy gradient was 0.05 kcal/mol/Å. The first 500 steps were performed with the steepest descent algorithm and the rest of the steps with the conjugate gradient algorithm.

(2) Calculating the molecular interaction fields (MIECs) for each peptide (11, 12). The MIECs for each residue-residue pair were computed using the MM/GB protocol. The MIECs included: (a) electrostatic (Columbic) interaction $\Delta G_{GB}$, (b) van der Waals interaction $\Delta E_{vdw}$, and (c) polar contribution to desolvation free energy $\Delta Gg_b$. The cutoff for calculating $\Delta E_{vdw}$ and $\Delta E_{ele_e}$ was set to 18.0 Å. A distance-independent interior dielectric constant of 1 was used to calculate $\Delta E_{ele}$. The charges used in the GB calculation were taken from the AMBER03 force field (37) and other GB parameters were taken from (39). The values of interior and exterior dielectric constants in the GB calculation were set to 1 and 80, respectively. In addition, the MIECs for the 9 residue pairs between the adjacent residues in ten-residue long peptides were also calculated to consider the conformational preference of the peptide. The molecular interaction component calculations, including read-in of the SH3/peptide complexes, definition of atom types in the GB calculation and assignment of the force field parameters, were automatically carried out using the gleap program in AMBER10 (40).

(3) Prediction of binding peptides using the MIEC-SVM model. Finally, the MIEC-SVM model was used to classify each peptide into binder and non-binder categories. The LIB-SVM program (41) was used in the predictions.

II. Peptide Microarray Measurement and Analysis

1. Peptide Microarray Screening

The GST-tagged Abl SH3 domain fusion protein was purified as previously described (12). Protein concentration was determined using the Bradford Assay (Bio-Rad). The purity of the fusion protein was checked by electrophoresis on SDS-PAGE gel and coomassie blue staining. The fusion protein was also subjected to electrophoresis on SDS-PAGE gel, followed by Western blot using a horseradish peroxidase-conjugated anti-GST antibody (Santa Cruz Biotechnology) and the SuperSignal West chemiluminescent substrate (Pierce).

All peptides were synthesized by Sigma-Aldrich. The peptides were printed onto glass slides in triplicates by ArrayIt Corporation. A buffer blank and a Cy3 marker were also printed in triplicates. The peptide arrays were blocked with the blocking buffer (5% non-fat dry milk, TBS pH8.0, 0.05% Tween 20) for an hour at room temperature. Next, the peptide arrays were incubated overnight at 4° C. with purified GST-Abl SH3 in the blocking buffer at a final concentration of 5 µM. After washing three times for ten minutes with the TBST buffer (TBS pH8.0, 0.05% Tween 20), an anti-GST antibody (Santa Cruz Biotechnology) was added to a final concentration of 0.2 µg/ml in the blocking buffer for one hour at room temperature. The arrays were then washed three times for ten minutes with the TBST buffer. Finally, the arrays were incubated with the secondary antibody, Cy3-conjugated goat-anti-mouse IgG (H+L) (Jackson ImmunoResearch), for one hour at room temperature, followed by washing for three times for ten minutes with the TBST buffer. As a control, the peptide array was incubated with the anti-GST and the secondary antibodies alone.

2. Analysis of Peptide Microarray Results

The peptide microarray was processed by the InnoScan 710 laser scanner (ArrayIt Corporation). Cy-3 fluorescence was detected using the 532 nm laser at 3 um resolution. The resulted microarray image was analyzed by the microarray image process software Mapix2.8.2 (ArrayIt Corporation). The fluorescent intensity of a microarray spot was defined as its own intensity minus the background intensity around it, as determined from the scanned image.

Results

A Pipeline to Predict Protein-peptide Interactions in the Human Proteome

To comprehensively identify interacting partners of the Abl1 protein, a systematic searching strategy was exploited (FIG. 1). All 69,404 peptides in the human proteome that contain the PxxP motif in the UniProt database (7) were first scored using a scoring matrix. This scoring matrix was generated using the Virtual Mutagenesis method previously developed (see details in (8)). Briefly, each amino acid of the peptide was mutated to the other 19 amino acids and the mutated complex structure was optimized using 2 ns molecular dynamics simulations. The difference in SH3-peptide binding free energy between the wild type and mutated peptides was calculated using the MM/PBSA method (9, 10) to represent how much an amino acid was preferred at each peptide position.

Next, the top 10,000 peptides ranked by the scoring matrix were analyzed and the conservation information was used to remove false positives. Because of functional constraints, the binding peptides of the Abl1 SH3 domain are more conserved across species than non-binding peptides. For each protein that contains at least one putative binder, multiple sequence alignment was generated across seven proteomes, including *Homo sapiens* (human), *Pan troglodytes* (chimpanzee), *Macaca mulatta* (rhesus macaque), *Mus musculus* (mouse), *Rattus norvegicus* (rat), *Canis familiaris* (dog) and *Bos taurus* (cow). Because the human Abl1 SH3 domain is completely conserved across these seven species, it is reasonable to assume that its interacting partners are also highly conserved. Therefore, those non-conserved peptides were removed from the candidate list. After applying the conservation filter, about half of the peptides were removed and 4981 peptides were left for further analysis.

The goal was to find the most confident interacting partners of Abl1 SH3 domain and the following procedure was used to further remove false positives. As illustrated in the previous studies (11, 12), each of these 4981 peptides in complex with the Abl1 SH3 domain was modeled and its molecular interaction energy components (MIECs) that reflect the energetic characteristics of the binding was calculated. Using the MIEC-SVM previously trained on 18 SH3 domains (12), each peptide was classified into binder or non-binder category. After this round of filtering, 1394 peptides in 714 proteins were predicted as binders of the Abl1 SH3 domain.

TABLE 1

The top 10 predicted binders (SEQ ID NOS 2-11, respectively in order of appearance) of the Abl1 SH3 domain

| Rank | Protein UniProt ID[a] | Position | Sequence | Score[b] |
|---|---|---|---|---|
| 1 | DOS_HUMAN | 497-506 | APAFPPPSPP | -3.24 |
| 2 | PRR12_HUMAN | 685-694 | PPAMPSPPPP | -3.24 |
| 3 | EVL_HUMAN | 185-194 | PPPPPVPPPP | -2.65 |
| 4 | WASF1_HUMAN | 347-356 | *TPPPPVPPPP* | -2.65 |
| 5 | WBP7_HUMAN | 438-447 | *PPPLPSPPPP* | -2.64 |
| 6 | WBP2_HUMAN | 167-176 | PPGYPYPPPP | -2.36 |
| 7 | SHAN3_HUMAN | 836-845 | *PPAFSPPPPP* | -1.40 |
| 8 | FMNL2_HUMAN | 549-558 | TPPMPPPPPP | -0.54 |
| 9 | WASP_HUMAN | 390-399 | *GPPMPPPPPP* | -0.54 |
| 10 | DIAP2_HUMAN | 561-570 | GPPPPPPAPP | -0.25 |

[a]The EVL peptide is known to interact with the Abl SH3 domain (in bold) (2); WASF1, WBP7, SHAN3 and WASP proteins are known to interact with the Abl protein (in italic bold) (42). [b]Score was calculated based on the PSSM reported in our previous study (8). This PSSM was generated by mutating the peptide residue at each position to all other 19 amino acids. Binding free energy difference between the wild type and mutated peptides was calculated to represent the preference of amino acids at a specific peptide position. The total score of the peptide was a sum of the score at each peptide position.

Among the top 10 predicted peptides shown in Table 1, five were from proteins known to interact with the Abl1 SH3 domain (in bold), including EVL that binds to the SH3 domain of Abl1. Considering how difficult such proteome-wide prediction is, a 50% (5/10) rate of identifying known interacting partners demonstrated a satisfactory performance of our approach. On the other hand, the remaining peptides may be new binders that have not been reported. To further refine the predictions, peptide microarray experiments were conducted on the predicted binding peptides to find the most reliable binders of the Abl1 SH3 domain.

Design of the Peptide Microarray and Control Experiments

To print peptide microarrays, method of immobilizing the peptides on the glass surface, as well as the amount of peptide printed, needed to decide. Therefore, 10 peptides were first selected to test out the conditions. These peptides included 4 known binders of the Abl1 SH3 domain (13, 14) and 6 non-binders (including 4 peptides that bind to other SH3 domains, but not Abl1 (13, 14), and 2 random peptides without the PxxP motif). Same as in the previous study (12), each peptide was 10-amino-acid long and two alanines were added at each end. A linker, either aminohexanoic acid (Ahx) or polyethylene glycol (PEG), was added at the N-terminus. The peptides were immobilized to the glass surface via the N-terminus. Two spot sizes, 150 um and 600 um in diameter, which corresponded to 1 nl and 5 nl of 0.3 mg/ml peptide solution dispensed to the array, were tested, respectively. Each printing amount and linker was tested in triplicates. To better quantitatively measure the signal intensity, fluorescence and laser scanner were used to detect the binding of the SH3 domain to the peptides, instead of chemiluminescence and film in the previous study (12). Briefly, GST-Abl SH3 fusion protein was purified and characterized as described before (12) (data not shown). Purified protein was overlaid onto the array, followed by incubation with an anti-GST antibody and then a Cy3-conjugated secondary antibody. Binding of GST-Abl SH3 to peptides generated a Cy3 fluorescent signal that was recorded on a laser scanner. The fluorescence intensity for each peptide was an average of triplicates.

Figure 2:
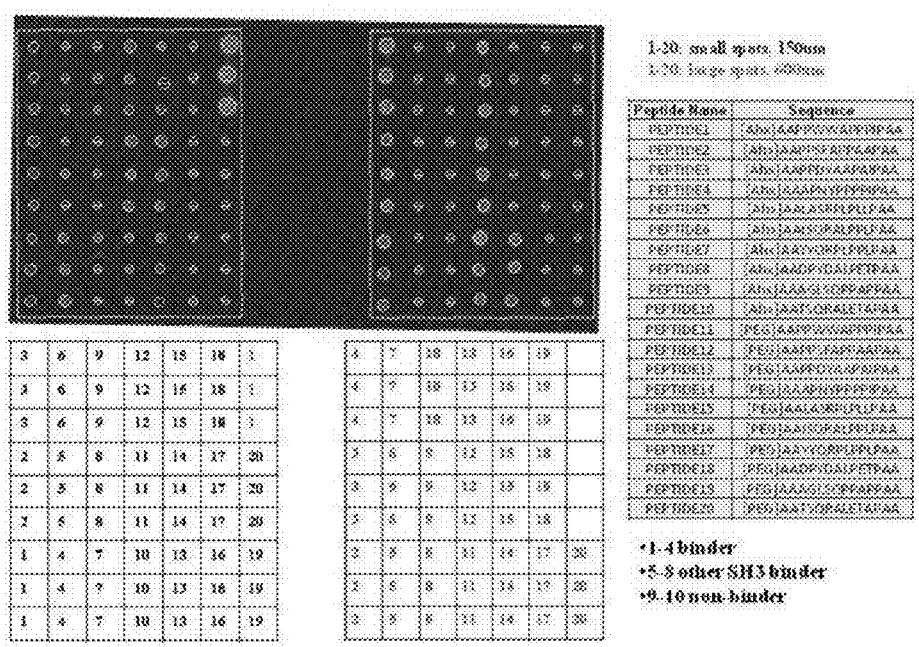
FIG. 2 illustrates binding of the Abl1 SH3 domain to ten testing peptides on the microarray. Ten peptides included 4 known binders and 6 non-binders (including 4 peptides that bind to other SH3 domains, but not Abl1, and 2 peptides without the PxxP motif). The upper left panel shows the fluorescence signals of the tested peptides on two microarrays with two printing amounts of the peptides. The bottom left panel shows the peptide positions on the microarray (black: small printing spots; red grey-scales: large printing spots). Two printing sizes of the peptides on the microarray and two linkers (aminohexanoic acid Ahx and polyethylene glycol PEG) at the N-terminal of these peptides that were attached to the glass surface (right panel) were tested.

FIG. 2 shows that the peptide microarray correctly distinguished binders from non-binders. By quantifying signal from each spot, it was found that there was no difference in signal intensity using either linker. As expected, the large spots generated much stronger overall signal than the small ones. However, the signal intensity was more even and the signal variation among triplicates was less in small spots than those in large spots. Hence the lower cost Ahx linker and 150 um spots were chosen for the rest of the experiments. As a control, the array was probed with anti-GST and the secondary antibodies alone and only basal levels of fluorescence were recorded (data not shown), demonstrating that there was no non-specific binding of these antibodies to the array.

Analysis of the Peptide Microarray Data

Figure 3:
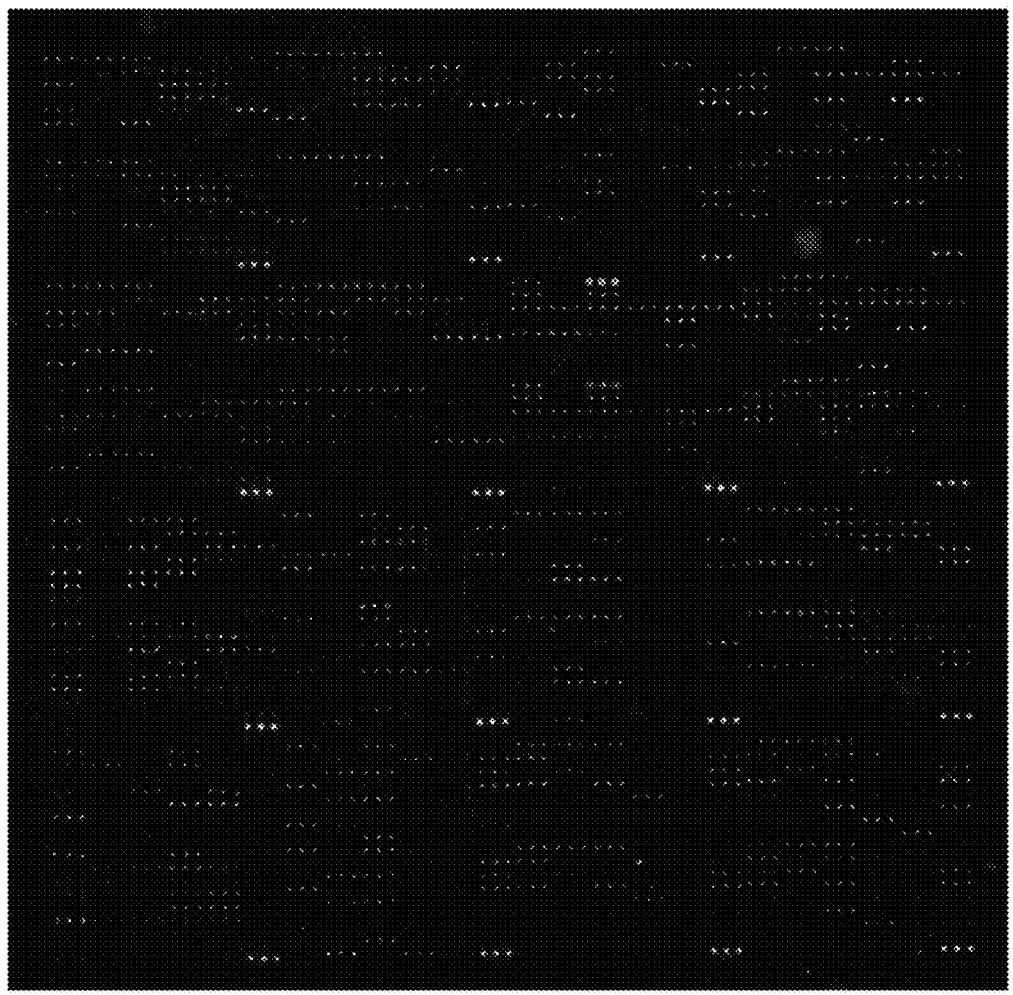
FIG. 3 illustrates binding of the Abl SH3 domain to 100 control (50 positives and 50 negatives) peptides and the top 700 predicted binders. Each peptide was printed on the microarray in triplicates.

In the production run, limited by the synthesis cost, the top 700 predicted binding peptides were synthesized and printed. 50 binders (including 38 with previously measured Kd's (13)) and 50 non-binders were also included on the array as positive and negative controls, respectively. The non-binders were randomly selected from the proteome, which are unlikely to interact with the Abl1 SH3 domain. Each peptide was printed in triplicates at two concentrations, 1 mg/ml and 0.5 mg/ml. The production array was probed the same way as the test run (FIG. 3). Similarly, a control experiment was done with just the antibodies and only basal levels of fluorescence were detected (data not shown).

Figure 4:
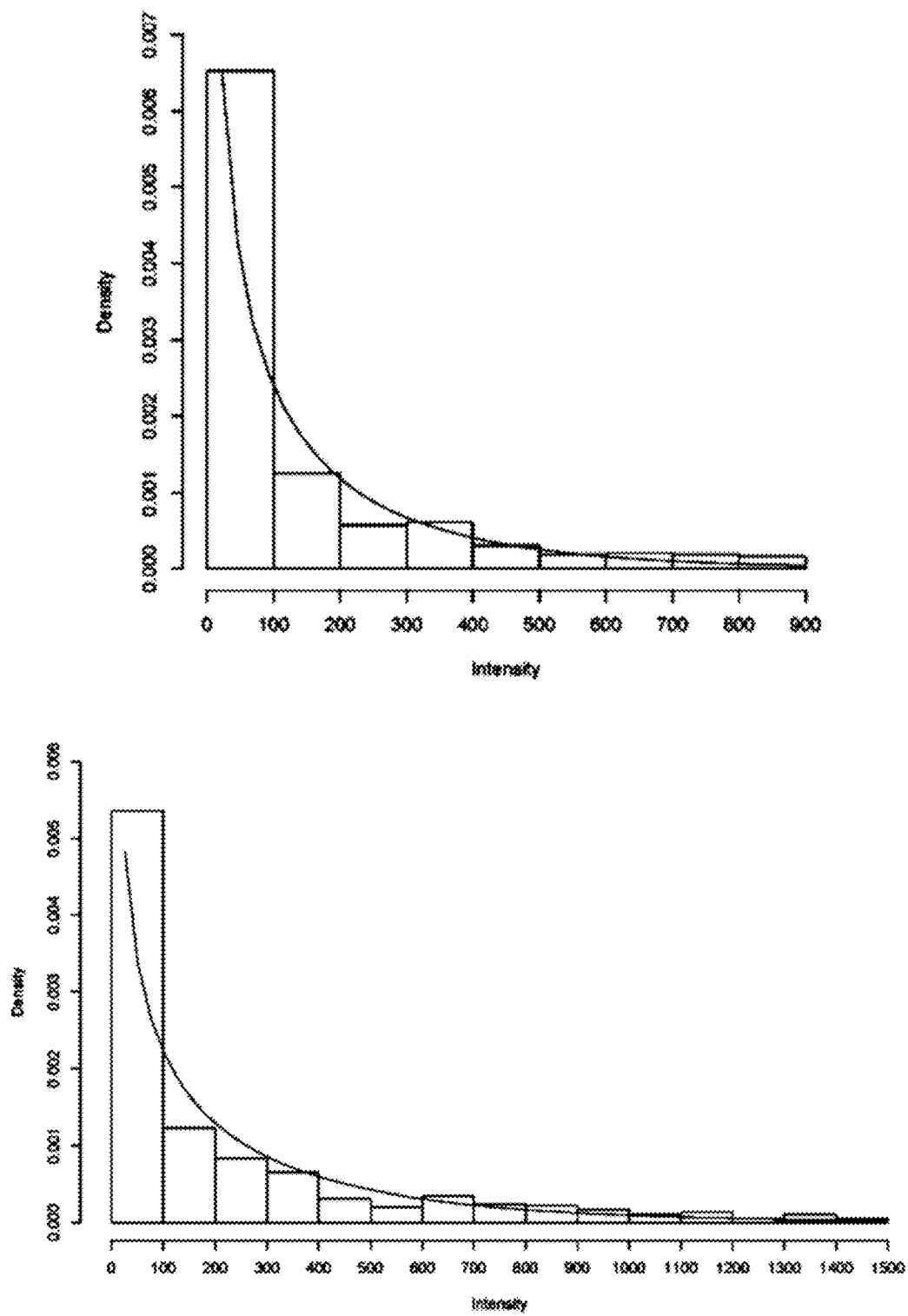
FIG. 4 provides modeling the distribution of fluorescence intensity in the peptide microarray experiment. Left and right: high and low printing amounts of peptides on the microarray.

To analyze the microarray data, the spots that were flagged as noisy were first removed. For the high (1 mg/ml) and low (0.5 mg/ml) printing concentrations, 724 and 767 (out of 800) spots remained for later analyses, respectively. Next, the statistical cut-off was determined for the significant fluorescence signal by modeling the background intensity distribution using a Gamma distribution (FIG. 4). The spots were binned based on the fluorescence intensity. To have a better curve fitting, the long tail of the histogram that represented strong binding peptides was removed and only the bins with intensity less than 900 and 1500 for the high and low concentrations, respectively, were kept. The model fitting and p-value calculation were conducted using R and P-value of 0.05 was used as the cutoff.

Figure 5:
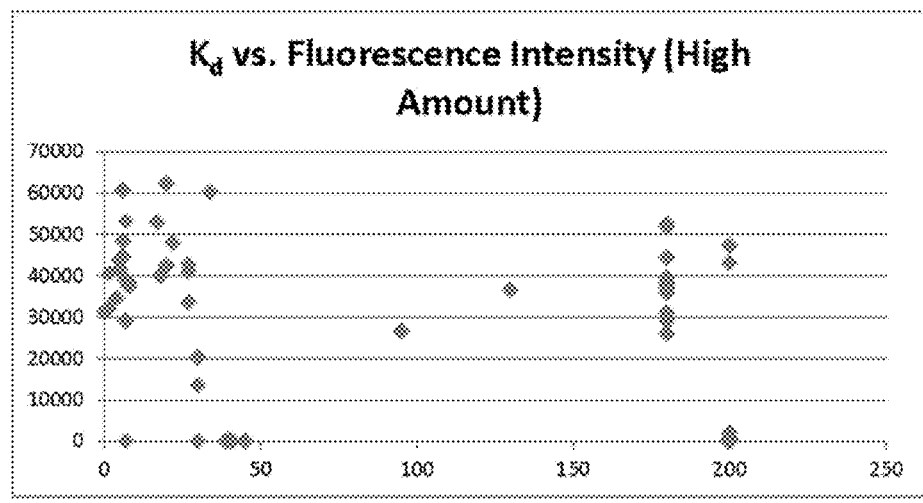
FIG. 5 illustrates the microarray binding measurement of the 100 control peptides. The X axis is the experimentally determined $K_d$ and the unit is μM. Y axis is the fluorescence intensity of microarray. The $K_d$ of the first 38 binding peptides is known. The rest 12 known binding peptides do not have a measured $K_d$. These 12 binders and the 50 non-binders were artificially assigned a Kd of 180 μM and 200 μM, respectively, for the illustration purpose. The florescence intensity of these peptides was an average of triplicates from the high printing concentration.

After establishing the parameters, the 100 control peptides were first examined and it was found that 40 from the 50 positive controls exhibited a strong signal and 48 from the 50 negative controls displayed only basal signal (FIG. 5). Therefore, the production array showed a satisfactory performance with a sensitivity of 0.80 (=40/50) and a specificity of 0.96 (=48/50). It is worth noting that the 10 false negative peptides were synthesized twice, and their binding to the Abl1 SH3 domain were tested using dot blot, only one of these 10 peptides showed signals (data not shown). Although these 10 peptides were reported to be binders, the experiments could not confirm this conclusion and the true sensitivity of the peptide microarray could be 0.98 (=40/41).

Figure 6:
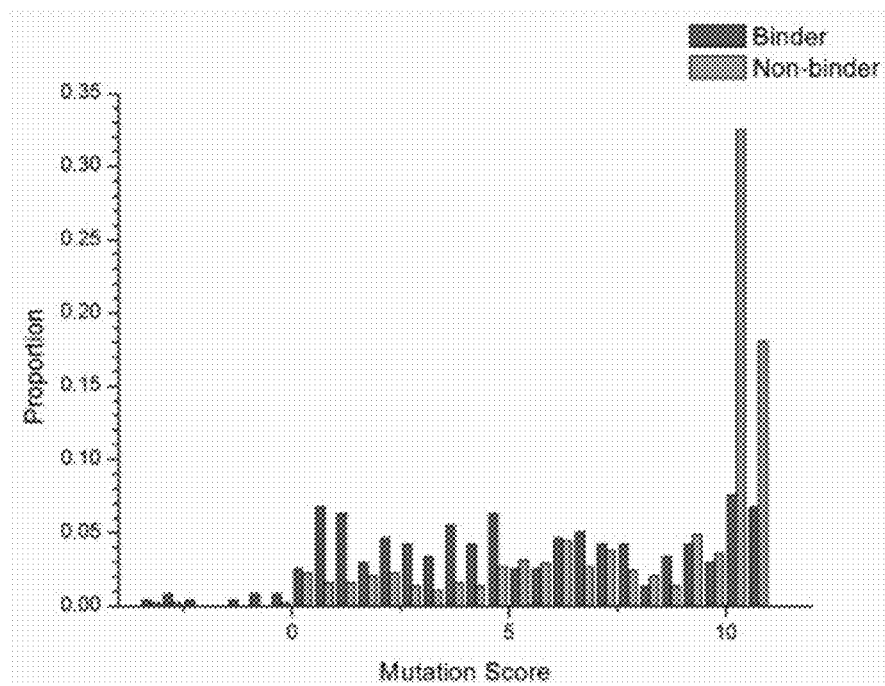
FIG. 6 provides the distributions of PSSM scores of the binders and non-binders in the 700 peptides.

The 700 predicted binders were then checked and 237 non-redundant peptides from 158 proteins were identified as putative binders, including 220 and 175 from high and low concentrations, respectively. When examining the PSSM scores of the 237 binding peptides and the remaining non-binding peptides, it was found that the binders have more favorable (smaller) PSSM scores than the non-binders although there is significant overlap between the two distributions (FIG. 6). This figure illustrates that the PSSM provides separation between binders and non-binders to some extent.

Among the identified binding peptides, 13 known binding partners of the Abl1 SH3 domain as well as 2 paralogs of the known binding partners (2) were found (Table 2). There are 52 proteins listed in (2) that interact with the Abl1 through SH3-peptide interaction and 25% (13/52) or 29% (15/52) of these manually curated interacting partners of the Abl1 SH3 domain were retrieved. Interestingly, six of them are also known substrates of the Abl1 kinase: ENAH, INPPL1, RAPH1, RIN1, WASF2 and WASL. In addition, the identified binding proteins also included another previously determined interacting partner of the SH3 domain that were not included in (2), SHIP2 (15), and a known substrate and interacting partner of Abl1, WASF3 (16). The interaction between Abl1 and its substrates is often mediated by SH3 domain (as in the case of the six substrates mentioned above). It is also known the interactions between WASF family proteins and Abl1 is mediated by SH3 domain (16). Therefore, WASF3 is likely to be a true interacting partner of the Abl1 SH3 domain. It is worth noting that there are numerous databases that document many partners of the Abl1 SH3 domain, but the curated list in (2) was only used as the gold standard for known interacting partners, which might miss quite a few true positives (like SHIP2). Given the challenge of proteome-wide identification of domain-peptide interactions, an 8.2% (13/158) rate of retrieving the curated interacting partners in this study was quite satisfactory while the other confirmed peptides may well be unknown binders.

TABLE 2

The known binding partners (SEQ ID NOS 12-33, respectively, in order of appearance) identified in this study.

| Protein | Start | End | Sequence | PSSM score | Average fluorescence intensity (high printing concentration) |
|---|---|---|---|---|---|
| 3BP1_HUMAN | 616 | 625 | APTVPPPLPP | 3.85 | 45057 |
| 3BP2_HUMAN | 201 | 210 | PPAYPPPPVP | 1.5 | 29708 |
| CBLB_HUMAN | 818 | 827 | PPSLPPPPPP | 2.35 | 35027 |
| CPSF6_HUMAN | 292 | 301 | LPPGPPPPVP | 4.22 | 1901 |
| ENAH_HUMAN | 357 | 366 | PNQVPPPPPP | 6.64 | 57981 |
| EVL_HUMAN | 185 | 194 | PPPPPVPPPP | -2.65 | 4678 |
| PDE4D_HUMAN | 81 | 80 | CPLQPPPPPP | 4.67 | 840 |
| RAPH1_HUMAN | 677 | 686 | SPPLPPPPPP | 0.66 | 17530 |
| RAPH1_HUMAN | 811 | 820 | APPTPPPPPP | 2.67 | 54434 |
| RIN1_HUMAN | 259 | 268 | PPAVPPPPVP | 4.76 | 42565 |
| SHIP2_HUMAN | 1050 | 1059 | PPDPPPPPLP | 3.77 | 58833 |
| VASP2_HUMAN | 165 | 174 | PPAGGPPPPP | 3.91 | 26163 |
| WASP2_HUMAN | 394 | 403 | PPPPPPPGPP | 1.01 | 2382 |
| WASL_HUMAN | 370 | 379 | PVAPPPPPPP | 2.72 | 48755 |
| WASL_HUMAN | 354 | 363 | APSGPPPPPP | 4.2 | 52347 |
| WASL_HUMAN | 371 | 380 | VAPPPPPPPP | 6.55 | 914 |
| WASL_HUMAN | 369 | 378 | GPVAPPPPPP | 7.01 | 44980 |
| WASL_HUMAN | 283 | 292 | SRGGPPPPPP | 10.76 | 744 |
| WASP_HUMAN | 390 | 399 | GPPMPPPPPP | -0.54 | 23425 |
| WASP_HUMAN | 363 | 372 | GRGGPPPPPP | 10.76 | 1297 |
| YLPM1_HUMAN | 81 | 90 | LPPPPLPPPP | 6.2 | 595 |
| YLPM1_HUMAN | 102 | 111 | PPPPPMPPPP | 6.54 | 22832 |

Note that CBLB and WASL are paralogs of CBL and WAS, respectively, which are known binding proteins of the Abl1 SH3 domain. The PSSM score was calculated in the same way as in Table 1.

The instant peptide microarray approach was also compared with another peptide array-based (SPOT array) method for detecting binding peptides of the Abl1 SH3 domain: only two known interacting partners (M4K1, DYN2), three paralogs of known interacting partners (SOS2, ABR and EFS) and one known substrate (SYNJ2) listed in (2) were discovered in Wu et al.'s study (17) (2.5%=2/81 recovering rate). The superior performance of the instant peptide microarray method demonstrates the power of integrating computational predictions and peptide microarray in identifying domain-peptide interactions in the human proteome.

Putative Novel Functions of Abl1 in Chromatin Modification and RNA Processing

The identified Abl1 binding peptides came from 158 proteins. To illustrate their functions, enrichment analysis of their gene ontology (GO) (18) annotations were performed using the DAVID software package (19) with the default parameters (Table 3). It is unsurprising that many proteins are related to actin cytoskeleton function, in which Abl1 is well known to be involved. Unexpectedly, putative binding partners that are involved in chromatin modification, RNA processing, transcriptional regulation and apoptosis were also found (Table 3). Interactions with these proteins suggested possible new functions of Abl1. Several interesting groups of putative interacting partners of Abl1 were highlighted in Table 4.

TABLE 3

Functions of the putative interacting proteins of Ab11 (p-value cutoff set to 1.0E.3)

| GO term | Number | Proteins (UniProt ID) | p-value |
|---|---|---|---|
| Cluster 1 | | | |
| actin cytoskeleton organization | 19 | FHDC1_HUMAN, EVL_HUMAN, WASF2_HUMAN, VASP_HUMAN, WASF3_HUMAN, WASF1_HUMAN, DIAP2_HUMAN, DAAM2_HUMAN, DAAM1_HUMAN, DIAP3_HUMAN, WASL_HUMAN, FMNL_HUMAN, FHOD3_HUMAN, WASP_HUMAN, FHOD1_HUMAN, FMN1_HUMAN, FMNL2_HUMAN, FMNL3_HUMAN, INF2_HUMAN | 3.1E−13 |
| actin filament-based process | 19 | FHDC1_HUMAN, EVL_HUMAN, WASF2_HUMAN, VASP_HUMAN, WASF3_HUMAN, WASF1_HUMAN, DIAP2_HUMAN, DAAM2_HUMAN, DAAM1_HUMAN, DIAP3_HUMAN, WASL_HUMAN, FMNL_HUMAN, FHOD3_HUMAN, WASP_HUMAN, FHOD1_HUMAN, FMN1_HUMAN, FMNL2_HUMAN, FMNL3_HUMAN, INF2_HUMAN | 9.5E−13 |
| cytoskeleton organization | 21 | TACC2_HUMAN, FHDC1_HUMAN, EVL_HUMAN, WASF2_HUMAN, VASP_HUMAN, CAP2_HUMAN, WASF3_HUMAN, WASF1_HUMAN, DIAP2_HUMAN, DAAM2_HUMAN, DAAM1_HUMAN, DIAP3_HUMAN, WASL_HUMAN, FMNL_HUMAN, FHOD3_HUMAN, WASP_HUMAN, FHOD1_HUMAN, FMN1_HUMAN, FMNL2_HUMAN, FMNL3_HUMAN, INF2_HUMAN | 3.4E−10 |
| Cluster 2 | | | |
| mRNA metabolic process | 14 | PR40B_HUMAN, SF3B4_HUMAN, WBP11_HUMAN, CPSF7_HUMAN, SF3B2_HUMAN, RBM16_HUMAN, SFR19_HUMAN, SFRS8_HUMAN, SF01_HUMAN, RBM22_HUMAN, CPSF6_HUMAN, KHDR3_HUMAN, SMN_HUMAN, MAPK2_HUMAN | 1.0E−5 |
| mRNA processing | 13 | PR40B_HUMAN, SF3B4_HUMAN, WBP11_HUMAN, CPSF7_HUMAN, SF3B2_HUMAN, RBM16_HUMAN, SFR19_HUMAN, SFRS8_HUMAN, SF01_HUMAN, RBM22_HUMAN, CPSF6_HUMAN, KHDR3_HUMAN, SMN_HUMAN | 1.3E−5 |
| RNA splicing | 11 | PR40B_HUMAN, SFR19_HUMAN, SFRS8_HUMAN, SF01_HUMAN, SF3B4_HUMAN, WBP11_HUMAN, PDCD7_HUMAN, RBM22_HUMAN, CPSF7_HUMAN, SF3B2_HUMAN, SMN_HUMAN | 1.1E−4 |
| RNA processing | 15 | PR40B_HUMAN, SF3B4_HUMAN, WBP11_HUMAN, PDCD7_HUMAN, CPSF7_HUMAN, NAF1_HUMAN, SF3B2_HUMAN, RBM16_HUMAN, SFR19_HUMAN, SFRS8_HUMAN, SF01_HUMAN, CPSF6_HUMAN, RBM22_HUMAN, KHDR3_HUMAN, SMN_HUMAN | 1.5E−4 |
| Cluster 3 | | | |
| chromatin modification | 10 | SET1A_HUMAN, SETD2_HUMAN, SET1B_HUMAN, UTY_HUMAN, DOT1L_HUMAN, CHD8_HUMAN, SMRC2_HUMAN, SMCE1_HUMAN, EP300_HUMAN, SMCA4_HUMAN | 4.2E−4 |
| Cluster 4 | | | |
| actin polymerization or depolymerization | 5 | EVL_HUMAN, WASL_HUMAN, WASP_HUMAN, WASF3_HUMAN, WASF1_HUMAN | 1.5E−5 |
| Cluster 5 | | | |
| transcription | 37 | SETD2_HUMAN, STF1_HUMAN, TAF1_HUMAN, PHF3_HUMAN, CHD8_HUMAN, FOXL2_HUMAN, ZBT12_HUMAN, ZFHX3_HUMAN, FOXB2_HUMAN, GBX2_HUMAN, SFR19_HUMAN, SET1B_HUMAN, SF01_HUMAN, WASL_HUMAN, CEBPA_HUMAN, ZN295_HUMAN, MED19_HUMAN, S2A4R_HUMAN, ZN628_HUMAN, HXD3_HUMAN, LBXCO_HUMAN, ASXL3_HUMAN, BCL9L_HUMAN, PO3F1_HUMAN, SMCA4_HUMAN, CMTA2_HUMAN, RBM16_HUMAN, ZFHX4_HUMAN, SET1A_HUMAN, SFRS8_HUMAN, ESX1_HUMAN, DIDO1_HUMAN, CRTC1_HUMAN, SMRC2_HUMAN, EP300_HUMAN, HXA10_HUMAN, KHDR3_HUMAN | 6.6E−6 |
| regulation of transcription | 37 | SETD2_HUMAN, STF1_HUMAN, TAF1_HUMAN, CHD8_HUMAN, RBM15_HUMAN, FOXL2_HUMAN, ZBT12_HUMAN, ZFHX3_HUMAN, FOXB2_HUMAN, GBX2_HUMAN, SET1B_HUMAN, SF01_HUMAN, WASL_HUMAN, | 6.3E−4 |

TABLE 3-continued

Functions of the putative interacting proteins of Ab11 (p-value cutoff set to 1.0E.3)

| GO term | Number | Proteins (UniProt ID) | p-value |
|---|---|---|---|
| | | CEBPA_HUMAN, ZN295_HUMAN, MED19_HUMAN, S2A4R_HUMAN, ZN628_HUMAN, LBXCO_HUMAN, HXD3_HUMAN, ASXL3_HUMAN, HME1_HUMAN, BCL9L_HUMAN, PO3F1_HUMAN, SMCA4_HUMAN, CMTA2_HUMAN, ZFHX4_HUMAN, SET1A_HUMAN, SFRS8_HUMAN, ESX1_HUMAN, CRTC1_HUMAN, SMRC2_HUMAN, SMCE1_HUMAN, EP300_HUMAN, HXA10_HUMAN, KHDR3_HUMAN, TULP4_HUMAN | |

TABLE 4

Putative interacting proteins (SEQ ID NOS 34-60, respectively, in order of appearance) of Ab11 involved in chromatin remodeling and transcriptional regulation.

| Protein Name (UniProt ID) | Start | End | Sequence | Mutation Score | Intensity | Function in UniProt(7) |
|---|---|---|---|---|---|---|
| ACINU_HUMAN | 1115 | 1124 | RPLHPPPPPP | 8.68 | 39304 | Component of a splicing-dependent multiprotein exon junction complex (EJC) deposited at splice junction on mRNAs |
| ASPP2_HUMAN | 866 | 875 | YPPYPPPPYP | 0.57 | 703 | Regulator that plays a central role in regulation of apoptosis and cell growth. Regulates TP53 by enhancing the DNA binding and transactivation function of TP53 on the promoters of proapoptosis genes in vivo. |
| ASXL3_HUMAN | 2028 | 2037 | PLALPPPPPP | 4.78 | 33982 | Putative Polycomb group (PcG) protein. |
| | 2034 | 2043 | PPPPPPPLPP | 1.1 | 13481 | |
| | 2033 | 2042 | PPPPPPPPLP | 1.47 | 6685 | |
| | 2031 | 2040 | LPPPPPPPPP | 0.12 | 1466 | |
| CHD8_HUMAN | 2232 | 2241 | LRAPGYPSSP | 10.34 | 7167 | Acts as a transcription repressor by remodeling chromatin structure and recruiting histone H1 to target genes. Suppresses p53/TP53-mediated apoptosis by recruiting histone H1 and preventing p53/TP53 transactivation activity. |
| DOT1L_HUMAN | 1591 | 1600 | RPPPPPPPPP | 4.12 | 15569 | Histone methyltransferase. Methylates 'Lys-79' of histone H3. |
| | 1590 | 1599 | TRPPPPPPPP | 7.56 | 7689 | |
| EP300_HUMAN | 930 | 939 | PLLPPQPATP | 10.53 | 7312 | Functions as histone acetyltransferase and regulates transcription via chromatin remodeling. |
| JMJD3_HUMAN | 767 | 776 | KPPPALPPPP | 10.41 | 672 | Demethylates trimethylated and dimethylated H3 'Lys-27.' |
| MBD5_HUMAN | 332 | 341 | PPQGPPPPPP | 3.8 | 41550 | Methyl-CpG-binding domain protein 5 |
| MBD6_HUMAN | 209 | 218 | APSPAPPPPP | 2.02 | 712 | Methyl-CpG-binding domain protein 6 |
| MED19_HUMAN | 24 | 33 | GPGKPPPPPP | 9.14 | 45927 | Component of the Mediator complex, a coactivator involved in the regulated transcription of nearly all RNA polymerase II-dependent genes. |
| PDCD7_HUMAN | 15 | 24 | PPPQPPPPAP | 5.04 | 51676 | Promotes apoptosis when overexpressed. |

TABLE 4-continued

Putative interacting proteins (SEQ ID NOS 34-60, respectively, in order of appearance) of Abl1 involved in chromatin remodeling and transcriptional regulation.

| | | | | | | |
|---|---|---|---|---|---|---|
| SET1A_HUMAN | 643 | 652 | PPEYPPPPPP | 8.35 | 36068 | Histone methyltransferase that specifically methylates 'Lys-4' of histone H3. |
| SET1B_HUMAN | 704 | 713 | PMPPPLPPPP | 9.47 | 1997 | Histone methyltransferase that specifically methylates 'Lys-4' of histone H3. |
| | 687 | 696 | PPPLPPPPPP | 0.66 | 1158.5 | |
| SETD2_HUMAN | 187 | 196 | PSSPPPPPPP | 10.61 | 49835 | Histone methyltransferase that specifically methylates 'Lys-36' of histone H3. |
| | 185 | 194 | SPPSSPPPPP | 4.53 | 31516 | |
| TAF1_HUMAN | 153 | 162 | CKLMPPPPPP | 6.91 | 7508 | Largest component and core scaffold of the TFIID basal transcription factor complex. |
| WBP7_HUMAN | 426 | 435 | PPLCPPPPPP | 2.97 | 45324 | Histone methyltransferase. Methylates 'Lys-4' of histone H3. |
| | 439 | 448 | PPLPSPPPPP | 2.64 | 20405 | |
| | 433 | 442 | PPPVSPPPLP | 4.13 | 16425 | |
| | 425 | 434 | PPPLCPPPPP | 0.41 | 8478 | |
| | 2250 | 2259 | RPAPPPPPPP | 4.72 | 6910 | |
| | 438 | 447 | PPPLPSPPPP | -2.64 | 1166 | |

Proteins are categorized based on their functions: chromatin modification (bold), binding to methylated DNA (highlighted in cyan), apoptosis (highlighted in green) and transcription and splicing (highlighted in yellow). Colors are shown in greyscales.

(1) Chromatin Remodeling Enzymes

Several methyltransferases are critical for transcription, for example, SET1A, SET1B and WBP7 methylate Lys4 of histone protein H3. Mono-, di- and tri-methylation of H3K4 (represented as H3K4me1, H3K4me2 and H3K4me3, respectively) are known to mark active promoters and enhancers (20). Besides the study, WBP7 was also found to interact with Abl1 SH3 domain in (17), although the function of this interaction is unclear.

The analysis revealed the binding of Abl1 to SETD2, a histone methyltransferase that methylates H3K36, which is a mark for transcription elongation and splicing (20). The SETD2 peptides (amino acid 185-194 and 187-196) are located in a proline rich region. Because this region does not contain any identified domain, it is likely the peptide is accessible for SH3 binding. SETD2 is known to interact with hyper-phosphorylated POLR2A, the RNA polymerase II (Pol II) large subunit that is also a substrate of Abl1. The observation implies possible recruitment of Abl1 by SETD2 to the proximity of the Pol II complex and thereby regulates transcription.

Another identified interacting partner of the Abl1 SH3 domain, DOT1, is a histone methyltransferase that methylates H3K79. H3K79me2 is a histone modification mark for transcribed regions (20). DOT1 also interacts with MLLT10, a myeloid/lymphoid or mixed-lineage leukemia protein. Confirmation of the interaction between Abl1 and MLLT10 and illustration of its functional importance are needed.

The analysis also revealed that Abl1 recognized peptides in JMJD3, a demethylase that demethylates repressive histone mark of H3K27me3 (20), as well as in EP300, an acetyltransferase that is a co-factor often located in enhancers (20). The other identified interacting partners involved in chromatin structure remodeling include a putative polycomb group protein, ASXL3 (21), and a chromatin modifier, CHD8 (22).

Additionally, it was found that Abl1 interacted with two methyl-CpG binding domain-containing proteins, MBD5 and MBD6. The functions of these two proteins are still largely unknown. Given Abl1's potential functions in modification of chromatin structure, it could play roles in DNA methylation since there exists interplay between histone modifications and DNA methylation (23, 24).

(2) Transcription and Splicing Complexes

In addition to these putative interactions between Abl1 and chromatin modification enzymes, the work showed that Abl1 SH3 domain also directly interacted with the transcription machinery, including TAF1, the largest component of the TFIID basal transcription factor complex (25) and MED19, a component of the Mediator complex and a co-activator involved in the regulated transcription of nearly all Pol II-dependent genes (26). Another putative Abl1 binder is ACINU, a component of the splicing-dependent multiprotein exon junction complex (EJC) deposited at splice junctions on mRNAs (27, 28). Many proteins involved in RNA splicing and mRNA processing were also identified (Table 3), which suggested novel functions of Abl1 in transcription and slicing regulation.

(3) Proteins Involved in Apoptosis

Two potential interacting proteins of Abl1 are known to be involved in apoptosis: PDCD7 promotes apoptosis when overexpressed (29); ASPP2 regulates p53 by enhancing the DNA binding and transactivation function of p53 on the promoters of pro-apoptotic genes in vivo (30). In addition, CHD8, a chromatin modifier and a putative Abl binder mentioned above, can suppress p53-mediated apoptosis by recruiting histone H1 and preventing p53 transactivation activity (31).

Discussion and Conclusion

The tyrosine kinase Abl1 is an important therapeutic target in hematopoietic malignancies. A systematic approach of combining computational predictions and peptide microarray was presented herewith to identify proteins bound to Abl1 via the SH3-peptide recognition in the human proteome. A comparison with the documented Abl1 interacting proteins showed a satisfactory performance of this approach. Given the complexity of protein interactions in human and the importance of determining such interactions for therapeutic development, the present approach holds great promise for proteome-wide search of binding partners of any disease-related protein. More excitingly, this kind of proteome-wide search reveals unknown functions of these proteins, as demonstrated. Putative interactions between Abl1 and numerous chromatin remodeling enzymes and RNA processing proteins were found, suggesting novel functions of Abl1 in chromatin modification and RNA regulation.

The instant computational approach provides a research tool that integrates computer modeling and bioinformatics analysis that provide complementary information to reduce false positives. Virtual Mutagenesis and MIEC-SVM calculations take into account conformational flexibility and energetic characteristics of the SH3-peptide interactions, while conservation analysis uses evolution information to remove noise in computer modeling. Thus, the instant approach better captures the structural and energetic features of protein recognition than pure bioinformatics analysis based on sequences only.

Because the transient and weak domain-peptide interactions are hard for immunoprecipitation in conjunction with mass spectrometry analysis, in vitro binding assay such as peptide (micro)array is often the first step to identify candidate peptides. Since the cost of peptide synthesis is still quite high, it is too expensive to include all possible peptides in the (micro)array. The more accurate the computational methods are, the more domain-peptide interactions could be identified in the follow-up experiments, as reflected by the much higher retrieving rate of known interacting partners of the Abl1 SH3 domain listed in (2) by the study than approaches without a computational component.

In the instant study, a peptide microarray platform that prints peptides onto the glass surface was employed. This technology uses much less peptides (in the order of pico mole) than the popular SPOT array (in the order of nano mole). Consequently, it also needs less protein, antibodies and other reagents than the SPOT array. In addition, peptide spots on the microarray are much smaller in size (150 um in diameter) than those on the SPOT array (around 3 mm in diameter), which allows high density printing on a very small surface. Hence screenings can be carried out in multiple replicates on a comprehensive scale and in a systemic way. The use of DNA/RNA oligo microarray slides in the assay also allows quantitative measurement by a microarray imager.

Signals on peptide microarrays can be detected using fluorescence, chemiluminescence or radioisotopes, whereas fluorescent dyes are somewhat problematic in SPOT arrays as the synthetic arrays show some background fluorescence (32). The quality-controlled synthesis of peptides reduces the number of false negatives due to lack of or poor-quality peptide on the spot, which may occur in the SPOT array. The same batch of pre-synthesized peptides can be used in thousands of microarray experiments as well as in various in-solution assays should there be a need. This not only saves cost but also takes out one variable in data interpretation. The power of our peptide microarray in detecting the weak SH3-peptide binding was first demonstrated in the validation experiment with 10 peptides in the test run and 100 control peptides in the production run. It was further demonstrated by a satisfactory correlation of the identified binders of the Abl SH3 domain to the documented known binders. Furthermore, measuring fluorescence intensity provides a quantitative signal that can be analyzed using statistical test to determine binding peptides.

References

1. Hantschel, O., and Superti-Furga, G. (2004) Regulation of the c-Abl and Bcr-Abl tyrosine kinases. *Nat Rev Mol Cell Biol* 5, 33-44.
2. Colicelli, J. (2010) ABL tyrosine kinases: evolution of function, regulation, and specificity. *Sci Signal* 3, re6.
3. Wong, S., and Witte, O. N. (2004) The BCR-ABL story: bench to bedside and back. *Annu Rev Immunol* 22, 247-306.
4. Neduva, V., and Russell, R. B. (2006) Peptides mediating interaction networks: new leads at last. *Curr Opin Biotechnol* 17, 465-471.
5. Perkins, J. R., Diboun, I., Dessailly, B. H., Lees, J. G., and Orengo, C. (2010) Transient protein-protein interactions: structural, functional, and network properties. *Structure* 18, 1233-1243.
6. Hilpert, K., Winkler, D. F., and Hancock, R. E. (2007) Peptide arrays on cellulose support: SPOT synthesis, a time and cost efficient method for synthesis of large numbers of peptides in a parallel and addressable fashion. *Nat Protoc* 2, 1333-1349.
7. UniProt, C. (2010) The Universal Protein Resource (UniProt) in 2010. *Nucleic Acids Res* 38, D142-148.
8. Hou, T., Chen, K., McLaughlin, W. A., Lu, B., and Wang, W. (2006) Computational analysis and prediction of the binding motif and protein interacting partners of the Abl SH3 domain. *PLoS Comput Biol* 2, e1.
9. Kollman, P. A., Massova, I., Reyes, C. M., Kuhn, B., Huo, S., Chong, L. T., Lee, M. R., Lee, T. S., Duan, Y., Wang, W., Donini, O., Cieplak, P., Srinivasan, J., Case, D. A., and Cheatham, T. E. (2000) Calculating structures and free energies of complex molecules: combining molecular mechanics and continuum models. *Accounts of Chemical Research* 33, 889-897.
10. Wang, W., Donini, O., Reyes, C. M., and Kollman, P. A. (2001) Biomolecular simulations: recent developments in force fields, simulations of enzyme catalysis, protein-ligand, protein-protein, and protein-nucleic acid noncovalent interactions. *Annu Rev Biophys Biomol Struct* 30, 211-243.
11. Hou, T., Zhang, W., Case, D. A., and Wang, W. (2008) Characterization of domain-peptide interaction interface: a case study on the amphiphysin-1 SH3 domain. *J Mol Biol* 376, 1201-1214.
12. Hou, T., Xu, Z., Zhang, W., McLaughlin, W. A., Case, D. A., Xu, Y., and Wang, W. (2009) Characterization of domain-peptide interaction interface: a generic structure-based model to decipher the binding specificity of SH3 domains. *Mol Cell Proteomics* 8, 639-649.
13. Pisabarro, M. T., and Serrano, L. (1996) Rational design of specific high-affinity peptide ligands for the Abl-SH3 domain. *Biochemistry* 35, 10634-10640.
14. Sparks, A. B., Rider, J. E., Hoffman, N. G., Fowlkes, D. M., Quillam, L. A., and Kay, B. K. (1996) Distinct ligand preferences of Src homology 3 domains from Src, Yes, Abl, Cortactin, p53 bp2, PLCgamma, Crk, and Grb2. *Proc Natl Acad Sci USA* 93, 1540-1544.
15. Wisniewski, D., Strife, A., Swendeman, S., Erdjument-Bromage, H., Geromanos, S., Kavanaugh, W. M., Tempst, P., and Clarkson, B. (1999) A novel SH2-containing phosphatidylinositol 3,4,5-trisphosphate 5-phosphatase (SHIP2) is constitutively tyrosine phosphorylated and associated with src homologous and collagen gene (SHC) in chronic myelogenous leukemia progenitor cells. *Blood* 93, 2707-2720.
16. Sossey-Alaoui, K., Li, X., and Cowell, J. K. (2007) c-Abl-mediated phosphorylation of WAVE3 is required for lamellipodia formation and cell migration. *J Biol Chem* 282, 26257-26265.
17. Wu, C., Ma, M. H., Brown, K. R., Geisler, M., Li, L., Tzeng, E., Jia, C. Y., Jurisica, I., and Li, S. S. (2007)

Systematic identification of SH3 domain-mediated human protein-protein interactions by peptide array target screening. *Proteomics* 7, 1775-1785.
18. Ashburner, M., Ball, C. A., Blake, J. A., Botstein, D., Butler, H., Cherry, J. M., Davis, A. P., Dolinski, K., Dwight, S. S., Eppig, J. T., Harris, M. A., Hill, D. P., Issel-Tarver, L., Kasarskis, A., Lewis, S., Matese, J. C., Richardson, J. E., Ringwald, M., Rubin, G. M., and Sherlock, G. (2000) Gene ontology: tool for the unification of biology. The Gene Ontology Consortium. *Nat Genet* 25, 25-29.
19. Huang da, W., Sherman, B. T., and Lempicki, R. A. (2009) Systematic and integrative analysis of large gene lists using DAVID bioinformatics resources. *Nat Protoc* 4, 44-57.
20. Li, B., Carey, M., and Workman, J. L. (2007) The role of chromatin during transcription. *Cell* 128, 707-719.
21. Schwartz, Y. B., and Pirrotta, V. (2007) Polycomb silencing mechanisms and the management of genomic programmes. *Nat Rev Genet* 8, 9-22.
22. Ho, L., and Crabtree, G. R. (2010) Chromatin remodelling during development. *Nature* 463, 474-484.
23. Edwards, J. R., O'Donnell, A. H., Rollins, R. A., Peckham, H. E., Lee, C., Milekic, M. H., Chanrion, B., Fu, Y., Su, T., Hibshoosh, H., Gingrich, J. A., Haghighi, F., Nutter, R., and Bestor, T. H. (2010) Chromatin and sequence features that define the fine and gross structure of genomic methylation patterns. *Genome Res* 20, 972-980.
24. Bartke, T., Vermeulen, M., Xhemalce, B., Robson, S. C., Mann, M., and Kouzarides, T. (2010) Nucleosome-interacting proteins regulated by DNA and histone methylation. *Cell* 143, 470-484.
25. Goodrich, J. A., and Tjian, R. (2010) Unexpected roles for core promoter recognition factors in cell-type-specific transcription and gene regulation. *Nat Rev Genet* 11, 549-558.
26. Malik, S., and Roeder, R. G. (2010) The metazoan Mediator co-activator complex as an integrative hub for transcriptional regulation. *Nat Rev Genet* 11, 761-772.
27. Tange, T. O., Shibuya, T., Jurica, M. S., and Moore, M. J. (2005) Biochemical analysis of the EJC reveals two new factors and a stable tetrameric protein core. *RNA* 11, 1869-1883.
28. Rigou, P., Piddubnyak, V., Faye, A., Rain, J. C., Michel, L., Calvo, F., and Poyet, J. L. (2009) The antiapoptotic protein AAC-11 interacts with and regulates Acinus-mediated DNA fragmentation. *EMBO J* 28, 1576-1588.
29. Park, E. J., Kim, J. H., Seong, R. H., Kim, C. G., Park, S. D., and Hong, S. H. (1999) Characterization of a novel mouse cDNA, ES18, involved in apoptotic cell death of T-cells. *Nucleic Acids Res* 27, 1524-1530.
30. Kampa, K. M., Bonin, M., and Lopez, C. D. (2009) New insights into the expanding complexity of the tumor suppressor ASPP2. *Cell Cycle* 8, 2871-2876.
31. Nishiyama, M., Oshikawa, K., Tsukada, Y., Nakagawa, T., Iemura, S., Natsume, T., Fan, Y., Kikuchi, A., Skoultchi, A. I., and Nakayama, K. I. (2009) CHD8 suppresses p53-mediated apoptosis through histone H1 recruitment during early embryogenesis. *Nat Cell Biol* 11, 172-182.
32. Frank, R. (2002) The SPOT-synthesis technique. Synthetic peptide arrays on membrane support—principles and applications. *J Immunol Methods* 267, 13-26.
33. Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs. *Nucleic Acids Res* 25, 3389-3402.
34. Chenna, R., Sugawara, H., Koike, T., Lopez, R., Gibson, T. J., Higgins, D. G., and Thompson, J. D. (2003) Multiple sequence alignment with the Clustal series of programs. *Nucleic Acids Res* 31, 3497-3500.
35. Xiang, Z. X., and Honig, B. (2001) Extending the accuracy limits of prediction for side-chain conformations. *Journal of Molecular Biology* 311, 421-430.
36. Case, D. A., Cheatham, T. E., Darden, T., Gohlke, H., Luo, R., Merz, K. M., Onufriev, A., Simmerling, C., Wang, B., and Woods, R. J. (2005) The Amber biomolecular simulation programs. *Journal of Computational Chemistry* 26, 1668-1688.
37. Duan, Y., Wu, C., Chowdhury, S., Lee, M. C., Xiong, G. M., Zhang, W., Yang, R., Cieplak, P., Luo, R., Lee, T., Caldwell, J., Wang, J. M., and Kollman, P. (2003) A point-charge force field for molecular mechanics simulations of proteins based on condensed-phase quantum mechanical calculations. *Journal of Computational Chemistry* 24, 1999-2012.
38. Hawkins, G. D., Cramer, C. J., and Truhlar, D. G. (1996) Parametrized models of aqueous free energies of solvation based on pairwise descreening of solute atomic charges from a dielectric medium. Journal of Physical Chemistry 100, 19824-19839.
39. Tsui, V., and Case, D. A. (2000) Molecular dynamics simulations of nucleic acids with a generalized born solvation model. *Journal of the American Chemical Society* 122, 2489-2498.
40. Zhang, W., Hou, T. J., Qiao, X. B., and Xu, X. J. (2004) Some basic data structures and algorithms for chemical generic programming. *Journal of Chemical Information and Computer Sciences* 44, 1571-1575.
41. Chang, C. C., and Lin, C. J. (2001) LIBSVM: a library for support vector machine. Software available at http://www.csie.ntu.edu.tw/~cjlin/libsvm.
42. Zanzoni, A., Montecchi-Palazzi, L., Quondam, M., Ausiello, G., Helmer-Citterich, M., and Cesareni, G. (2002) MINT: a Molecular INTeraction database. *FEBS-Lett* 513, 135-140.

Example 2

The Recognition of Methylated Peptides by *Drosophila melanogaster* Polycomb Chromodomain Abstract Lysine methylation is one of the important post-translational modifications (PTMs) that regulate protein functions. Up to date, proteomic identification of this PTM remains a challenge due to the lack of effective enrichment methods in mass spectrometry experiments. To address this challenge, a systematic approach was presented here to predicting peptides in which lysine residues may be methylated to mediate protein-protein interactions. The chromodomain of the Polycomb protein in *D. melanogaster* was used as a model system to illustrate the success of this approach. The molecular dynamics simulations and free energy analyses were started on the histone peptides complexed with the Polycomb chromodomain to understand how the binding specificity is achieved. Next, virtual mutagenesis was conducted to quantify each domain and peptide residue's contribution to the domain-peptide recognition, based on which scoring scheme was developed to evaluate the possibility of any lysine-containing peptides to be methylated and recognized by the chromodomain. A peptide microarray experiment on a panel of conserved histone peptides showed a satisfactory prediction accuracy of the scoring scheme. Further, a bioinformatics pipeline that integrates multiple lines of evidences including conservation, sub-cellular localization and mass spectrometry data, were implemented to scan the fly proteome for a systematic identification of possible methyllysine-containing peptides. These putative chromodomain-binding peptides suggest unknown functions of the important regulator protein Polycomb and provide a list of candidate methylation events for follow-up investigations.

Introduction

Proteins can exhibit specificity in their binding to methylated lysines—the *Drosophila melanogaster* protein Polycomb, a member of the chromodomain group of proteins that regulate chromatin structure and that are involved with genetic repression[1], binds strongly to trimethylated Lys27 of histone protein H3 (H3K27me3) but only weakly to trimethylated H3K9[2,3]. Post-translational methylation has has also been found on proteins other than histone peptides. The expression of the transient protein p53, for instance, which is involved in tumor suppression, is regulated by lysine methylation effected by the writer protein Set9[4]. In addition, proteins that interact with histones can themselves be marked by lysine methylation, which can affect their interactions with histone peptides[5]. While very little is known about the ability of chromodomain proteins to recognize methylated lysines on non-histone peptides, the Polycomb-group protein (PcG) Pc2 has been observed to interact with lysine residues modified by attachment of a small ubiquitin-like modifier (SUMO)[6,7]. This phenomenon suggests that PcGs could have functions of interest that are currently unknown besides genetic regulation by modified histone recognition.

Mass-spectrometry experiments can detect many types of post-translation modifications (PTMs) and the proteins that manipulate them, but its use in the specific case of methylation is limited due to the narrow peak differential in the spectrum. In theory, binding assay experiments can determine the binding affinity of a protein to a wide variety of methylated-lysine peptides, but the experimental data has been scarce. By combining a computational study with a scan of the fruit fly's proteome, both the total class of proteins that can interact with methylated lysine and the methylated-lysine peptides that can be recognized by PcG proteins are identified, and a more complete understanding of the functions of this group of proteins is acquires.

Results

I. Overall Procedure

Figure 7:
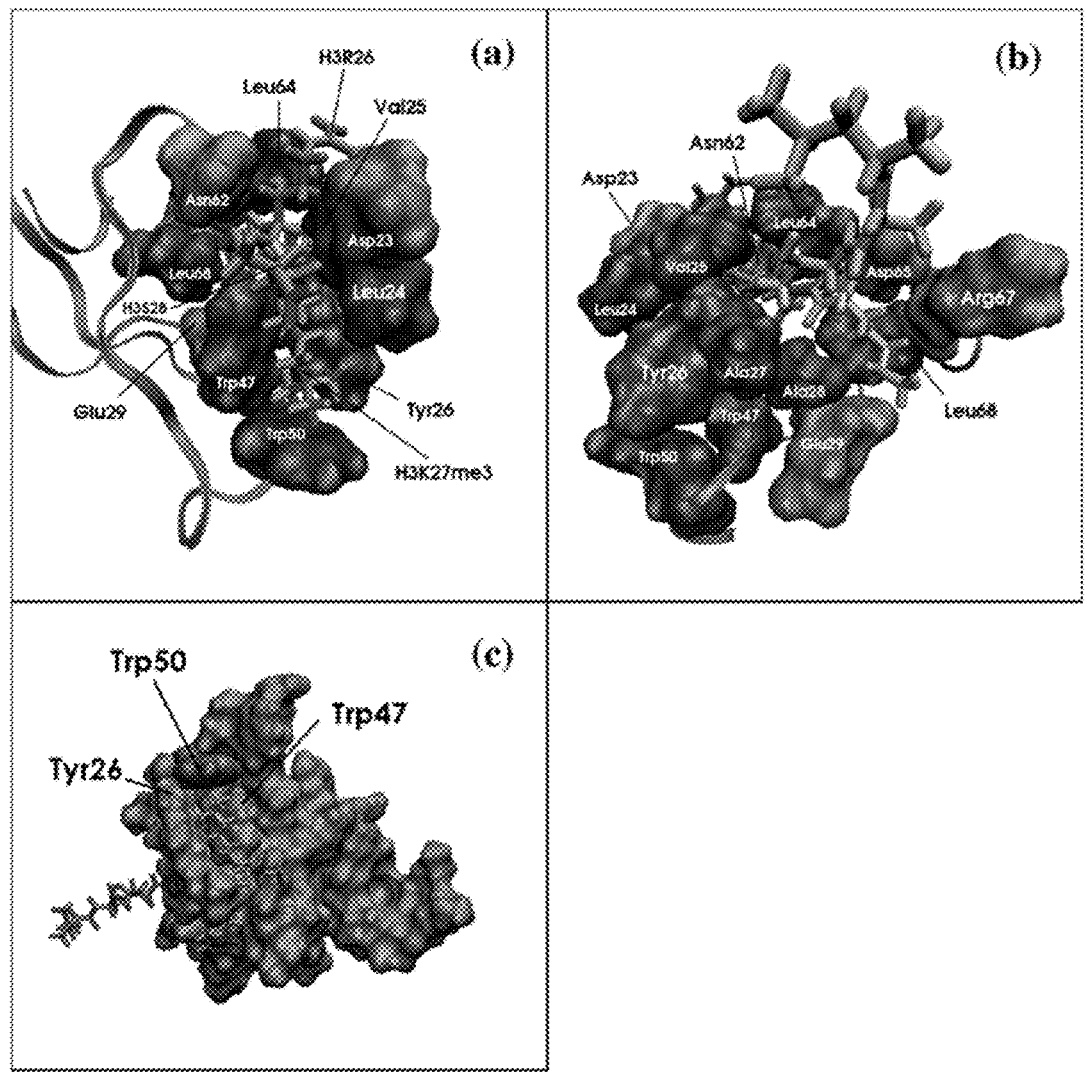
FIG. 7 provides the Polycomb/H3K27me3 complex. (a, frontal view; b, back view) Only residues in Polycomb critical to binding to H3 are shown. Hydrophobic residues are shown in greyscales of brown; acidic residues, in orange; basic residues, in turquoise, and polar residues, in violet. The backbone of the remainder of Polycomb is shown by a green ribbon, and H3 by a licorice model. H3R26 is shown in red; H3K27me3, in orange; H3S28, in yellow; H3A24 and H3A25, in magenta; and H3L20 through H3K23 in light blue. (c) Orthographic view of the Polycomb/H3K27me3 complex. The Polycomb protein is shown by molecular surface rendering, and all residues are green except for Tyr26, Trp47 and Trp50, which are lime green, sea green and olive green, greyscales respectively. H3 is shown by licorice model; H3R26 is orange while H3K27me3 is yellow, and the rest of H3 is gray. Images generated by VMD[66].
Figure 8:
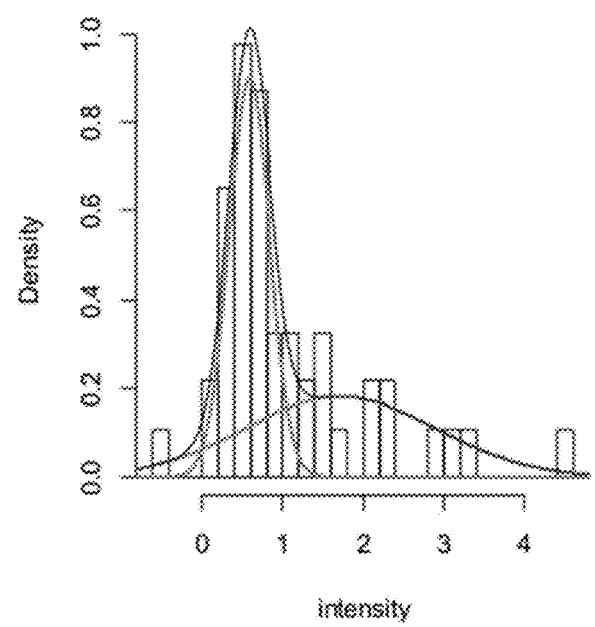
FIG. 8 illustrates a mixed gaussian fit of microarray data of Polycomb protein chromodomain binding to histone H3/H4 peptides (black: overall; blue: non-binding background distribution; red: binding distribution). Colors shown in greyscales.

Molecular dynamics (MD) simulations were performed on *Drosophila melanogaster* Polycomb protein complexed with a peptide from the histone protein H3. First, the binding affinities of wild-type Polycomb to unmodified H3 and H3K27me1, H3K27me2, and H3K27me3 were determined by simulations and free-energy calculation. The models were derived from crystal structures; the structures of the Polycomb-H3 complexes are shown in FIG. 7. The contributions of each individual residue in both Polycomb and H3 to the binding interaction were derived by energy decomposition analysis (see Materials and Methods), leading to the discovery of the most critical Polycomb residues. Next, mutation matrices were formed both for Polycomb and for H3 to estimate the effect of point mutation in each residue critical for binding. Subsequently, peptide microarray binding data were used to verify the prediction of binding to Polycomb on fly histone peptides, which demonstrated the satisfactory prediction ability for the H3 mutation matrix. Finally, a scan of the fruit fly proteome was conducted to find additional peptides with methylated lysine and estimate their binding affinity relative to the wild-type H3 peptide by using the mutation matrix. A further refinement was conducted through a combined analysis of data from conservation, sub-cellular location, and mass spectrometry evidence. The final list of possible Polycomb binders provided insight into the quantity and character of proteins that can interact with Polycomb.

II. Simulation Results

A. Residues in Polycomb Protein Critical for Binding to H3

Having determined that $\in=4.0$ is the optimal dielectric constant for deriving accurate binding energies with this model (see Materials and Methods, subsection D), residue decomposition[8] was performed on the Polycomb/H3K27me3 complex for this value. The results of this calculation are given in Table I.

TABLE I

Polycomb-H3 Binding Free Energy Residue Decomposition.
The residue Lys48 is included since, although its net contribution is only −0.13 kcal/mol, the van der Waals component to that contribution is relatively high at −0.71 kcal/mol.
Table I discloses "H3L20 to H3S28" as SEQ ID NO: 88, "Asp23 to Ala28" as SEQ ID NO: 128 and "Asn62 to Asp65" as SEQ ID NO: 129

| Residue | Contrib. in Polycomb/ H3K27me3 |
|---|---|
| H3L20 | −0.08 ± 0.54 |
| H3A21 | −0.50 ± 0.20 |
| H3T22 | −1.78 ± 0.42 |
| H3K23 | −6.66 ± 0.56 |
| H3A24 | −4.27 ± 0.33 |
| H3A25 | −5.41 ± 0.53 |
| H3R26 | −8.41 ± 0.64 |
| H3K27me3 | −13.69 ± 0.67 |
| H3S28 | −2.09 ± 0.67 |
| Asp23 | −1.82 ± 0.56 |
| Leu24 | −2.57 ± 0.36 |
| Val25 | −3.29 ± 0.26 |
| Tyr26 | −4.82 ± 0.42 |
| Ala27 | −1.69 ± 0.22 |
| Ala28 | −1.89 ± 0.26 |
| Glu29 | −1.22 ± 0.34 |
| Trp47 | −5.08 ± 0.42 |
| Lys48 | −0.13 ± 0.26 |
| Trp50 | −2.36 ± 0.20 |
| Tyr54 | −0.68 ± 0.12 |
| Thr56 | −1.32 ± 0.12 |
| Glu58 | −1.18 ± 0.72 |
| Pro59 | −0.64 ± 0.06 |
| Asn62 | −3.15 ± 0.55 |
| Ile63 | −1.14 ± 0.13 |
| Leu64 | −2.84 ± 0.24 |
| Asp65 | −2.59 ± 0.19 |
| Arg67 | −1.95 ± 0.53 |
| Leu68 | −2.26 ± 0.25 |
| Glu73 | −0.61 ± 0.02 |

The two most important residues in Polycomb for the binding interaction are Tyr26 (−4.82 kcal/mol) and Trp47 (−5.08 kcal/mol), which are two of the three bulky hydrophobic residues that form a hydrophobic cage for van der Waals attraction of H3K27me3. The third residue of the cage, Trp50, is also high on the critical residue list (−2.36 kcal/mol). Other key hydrophobic residues in Polycomb for the interaction are Leu24 (−2.57 kcal/mol), Val25 (−3.29 kcal/mol), Leu64 (−2.84 kcal/mol) and Leu68 (−2.26 kcal/mol), while the most important charged Polycomb residues are Asp23 (−1.82 kcal/ mol), Glu29 (−1.22 kcal/mol), Glu58 (−1.18 kcal/mol), Asp65 (−2.59 kcal/mol), and Arg67 (−1.95 kcal/mol). A crucial neutral polar residue is Asn62 (−3.15 kcal/mol). Apart from H3K27me3 (−13.69 kcal/mol), the most important residues in H3 for the binding interaction are H3R26 (−8.41 kcal/mol), H3K23 (−6.66 kcal/mol), H3A25 (−5.41 kcal/mol), H3A24 (−4.27 kcal/mol), H3S28 (−2.09 kcal/mol), and H3T22 (−1.78 kcal/mol). The most important electrostatic interactions in the Polycomb/H3 complex, from visualization of the trajectory, are Asp23 with H3R26; Glu29 with H3K23; Glu58 with H3S28; and Asp65 with H3K23.

B. Polycomb Protein Mutation Matrix

The mutation matrix for the Polycomb protein in complex with H3K27me3 is provided. The following observations can be made about trends in the mutation matrix. First, mutations of the 8 or 9 residues in Polycomb (Tyr26, Trp47, Val25, Asn62, Leu64, Asp65, Leu24, Trp50, and possibly Arg67) that are most important to the binding interaction generally weaken the binding affinity, especially in the case of Trp47. Second, mutations in the lower half of the matrix (residues less critical for binding) tend to make the interaction with H3K27me3 more favorable, with the exception of Glu58. Third, mutations to positively charged amino acids (lysine and arginine) as well as to glycine, proline, and to a lesser extent, alanine, tend to make the binding interaction more unfavorable. Finally, mutations to negatively charged residues (aspartic and glutamic acid) tend to make the binding interaction more favorable.

C. Histone H3 Peptide Mutation Matrix

Three aspects of this problem are particularly worthy of investigation; first, to find polypeptides other than histones that contain methylated lysine; second, to understand the mechanisms by which a chromodomain protein recognizes a peptide containing a methylated lysine residue, and finally, to obtain as much functional information as possible about the polypeptides that bind to chromodomain protein. Therefore, in another set of simulations, point mutations were performed on residues of the H3 peptide in turn (positions 20 to 28, except for H3K27me3 which was kept conserved) while the Polycomb protein was held to the wild-type. In general, mutations of peptide residues tend to have a more favorable effect on the binding interaction than mutations of Polycomb residues, especially those which are foremost in importance for binding to H3. Several trends are evident from the mutation matrix data: first, mutations of H3R26 tend to have a weakening effect on the binding affinity; second, that mutations of H3A25 tend to make the binding interaction more favorable; third, mutations of H3 residues to Gly, Asp, Asn, and Pro make the binding energy more unfavorable, especially in the near vicinity of H3K27me3; and fourth, mutations of H3 residues to tyrosine and tryptophan have a strengthening effect on the binding interaction.

III. Experimental Validation of Theoretical Predictions

A. Experimental Identification of Binders

There are a total of 46 histone peptide sequences (9 a.a. long) with a single lysine-trimethylation site which are conserved between the human and fruit fly H2, H3 and H4 proteins (Table II). These were screened for Polycomb protein chromodomain binding by peptide microarray. Each peptide sequence was screened as triplets, and the fluorescence intensity was quantified with background subtraction individually for each spot from the microarray images by ImageJ[9] and the whole data set was fit to a mixed Gaussian distribution model (FIG. 8, Table III).

TABLE II

| Uniprot ID | Lysine Site | Sequence | SEQ ID NO: | PWM score | Prediction | Array Verification |
|---|---|---|---|---|---|---|
| sp\|P08985\|H2AV_DROME | 115 | GVIPHIHKS | 61 | −21.83 | Binder | NonBinder |
| sp\|P08985\|H2AV_DROME | 37 | GRIHRHLKS | 62 | −19.28 | Binder | Binder |
| sp\|P02299\|H3_DROME | 56 | REIRRYQKS | 63 | −18.11 | Binder | Binder |
| sp\|P84040\|H4_DROME | 20 | GGAKRHRKV | 64 | −16.8 | Binder | Binder |
| sp\|P02283\|H2B_DROME | 43 | IYIYKVLKQ | 65 | −16.55 | Binder | NonBinder |
| sp\|P84040\|H4_DROME | 79 | YTEHAKRKT | 66 | −15.13 | Binder | NonBinder |
| sp\|P84051\|H2A_DROME | 118 | QAVLLPKKT | 67 | −12.23 | Binder | NonBinder |
| sp\|P02283\|H2B_DROME | 82 | SRLAHYNKR | 68 | −12.2 | Binder | NonBinder |
| sp\|P02299\|H3_DROME | 64 | STELLIRKL | 69 | −11.17 | Binder | NonBinder |
| sp\|P84040\|H4_DROME | 77 | VTYTEHAKR | 70 | −10.7 | Binder | NonBinder |
| sp\|P84051\|H2A_DROME | 117 | IQAVLLPKK | 71 | −9.6 | Binder | Binder |
| sp\|P02299\|H3_DROME | 115 | NLCAIHAKR | 72 | −9.58 | Binder | NonBinder |
| sp\|P02283\|H2B_DROME | 105 | LLPGELAKH | 73 | −7.58 | Binder | NonBinder |
| sp\|P08985\|H2AV_DROME | 13 | GKDSGKAKA | 74 | −7.14 | Binder | NonBinder |

TABLE II-continued

| Uniprot ID | Lysine Site | Sequence | SEQ ID NO: | PWM score | Prediction | Array Verification |
|---|---|---|---|---|---|---|
| sp\|P84040\|H4_DROME | 59 | EETRGVLKV | 75 | -4.62 | Binder | NonBinder |
| sp\|P02299\|H3_DROME | 23 | PRKQLATKA | 76 | -3.42 | Binder | Binder |
| sp\|P02299\|H3_DROME | 9 | RTKQTARKS | 77 | -2.66 | Binder | Binder |
| sp\|P84249\|H33_DROME | 37 | PSTGGVKKP | 78 | -2.26 | Binder | NonBinder |
| sp\|P84051\|H2A_DROME | 35 | RIHRLLRKG | 79 | -1.24 | Binder | Binder |
| sp\|P84051\|H2A_DROME | 73 | GNAARDNKK | 80 | -1.06 | Binder | NonBinder |
| sp\|P08985\|H2AV_DROME | 74 | ELAGNASKD | 81 | -1.04 | Binder | NonBinder |
| sp\|P02299\|H3_DROME | 18 | TGGKAPRKQ | 82 | -0.88 | Binder | NonBinder |
| sp\|P84051\|H2A_DROME | 94 | RNDEELNKL | 83 | -0.65 | Binder | NonBinder |
| sp\|P02299\|H3_DROME | 79 | REIAQDFKT | 84 | -0.64 | Binder | NonBinder |
| sp\|P08985\|H2AV_DROME | 79 | ASKDLKVKR | 85 | -0.57 | Binder | Binder |
| sp\|P02283\|H2B_DROME | 117 | EGTKAVTKY | 86 | -0.41 | Binder | Binder |
| sp\|P02299\|H3_DROME | 37 | PATGGVKKP | 87 | -0.08 | Binder | NonBinder |
| sp\|P02299\|H3_DROME | 27 | LATKAARKS | 88 | 0 | Binder | Binder |
| sp\|P08985\|H2AV_DROME | 101 | EELDSLIKA | 89 | 0.4 | NonBinder | NonBinder |
| sp\|P84040\|H4_DROME | 44 | LARRGGVKR | 90 | 1.25 | NonBinder | NonBinder |
| sp\|P84040\|H4_DROME | 91 | MDVVYALKR | 91 | 1.88 | NonBinder | Binder |
| sp\|P84040\|H4_DROME | 16 | GLGKGGAKR | 92 | 2.78 | NonBinder | NonBinder |
| sp\|P08985\|H2AV_DROME | 120 | IHKSLIGKK | 93 | 3.14 | NonBinder | NonBinder |
| sp\|P08985\|H2AV_DROME | 15 | DSGKAKAKA | 94 | 4.51 | NonBinder | Binder |
| sp\|P84051\|H2A_DROME | 74 | NAARDNKKT | 95 | 5.12 | NonBinder | NonBinder |
| sp\|P02283\|H2B_DROME | 54 | PDTGISSKA | 96 | 5.17 | NonBinder | NonBinder |
| sp\|P84249\|H33_DROME | 36 | APSTGGVKK | 97 | 5.21 | NonBinder | NonBinder |
| sp\|P02299\|H3_DROME | 36 | APATGGVKK | 98 | 6.53 | NonBinder | NonBinder |
| sp\|P02283\|H2B_DROME | 113 | HAVSEGTKA | 99 | 7.24 | NonBinder | NonBinder |
| sp\|P84040\|H4_DROME | 31 | DNIQGITKP | 100 | 7.81 | NonBinder | NonBinder |
| sp\|P02299\|H3_DROME | 122 | KRVTIMPKD | 101 | 7.85 | NonBinder | NonBinder |
| sp\|P08985\|H2AV_DROME | 11 | KAGKDSGKA | 102 | 9.57 | NonBinder | NonBinder |
| sp\|P08985\|H2AV_DROME | 77 | GNASKDLKV | 103 | 12.19 | NonBinder | NonBinder |
| sp\|P02299\|H3_DROME | 14 | ARKSTGGKA | 104 | 20.66 | NonBinder | NonBinder |
| sp\|P84040\|H4_DROME | 12 | KGGKGLGKG | 105 | 21.28 | NonBinder | NonBinder |
| sp\|P08985\|H2AV_DROME | 7 | MAGGKAGKD | 106 | 24.61 | NonBinder | NonBinder |

TABLE III

Mixed gaussian fitting parameters of microarray data of polycomb protein chromodomain binding to H3 and H4 peptides

| Polycomb-H3/H4 | Gaussian Distribution G1 (Non-Binding background) | Gaussian Distribution G1 (Binding) |
|---|---|---|
| Proportion (%) | 0.5722818 | 0.4277182 |
| Mean (μ) | 0.5849581 | 1.7184761 |
| Standard Deviation (σ) | 0.2535892 | 1.1745391 |

A sequence was identified as a positive binder when at least two out of the three microarray spots exhibited a fluorescence intensity that made a p-value cutoff of 0.001 from the background Gaussian distribution in the mixed model. Twelve out of the 46 sequences were identified as positive binders under these criteria. Ten of these microarray-identified binders also yielded high mutation matrix score in an independent prediction (Table IV).

TABLE IV

Identified histone binders for Polycomb protein chromodomain

| SEQ ID NO: | Sequence | Histone (on human histone) | Lysine site |
|---|---|---|---|
| 62 | GRIHRHLKS | H2AZ | 37 |
| 64 | GGAKRHRKV | H4 | 20 |
| 71 | IQAVLLPKK | H2A1, H2AX, H2A3, H2A1D, H2A2C, H2A2A, H2A1B, H2A1C, H2A1J, H2A2B, H2A1A, H2A1H, H2AJ | 117 |
| 77 | RTKQTARKS | H3.3 | 9 |
| 79 | RIHRLLRKG | H2A1A | 35 |
| 86 | EGTKAVTKY | H2B1A, H2B1B, H2B1C, H2B1D, H2B1H, H2B1J, H2B1K, H2B1M, H2B1L, H2B1N, H2B1O, H2B2E, H2B2F, H2B3B, H2BFS | 117 |
| 88 | LATKAARKS | H3.3 | 27 |
| 91 | MDVVYALKR | H4 | 91 |
| 76 | PRKQLATKA | H3.3 | 23 |
| 94 | DSGKAKAKA | H2AV | 15 |
| 85 | ASKDLKVKR | H2AZ, H2AV | 79 |
| 63 | REIRRYQKS | H3.3 | 56 |

B. Prediction Performance of Polycomb Mutation Matrix on Fly Histone Peptides

For a thorough and critical assessment of the prediction performance of the mutation matrix, microarray was used to test the binding between Polycomb and the 28 histone peptides that it was predicted to bind to, as well as 18 peptides that were not predicted to bind. By doing this, both true positive and true negative can be identified and a comprehensive analysis of prediction performance is feasible.

Figure 9:
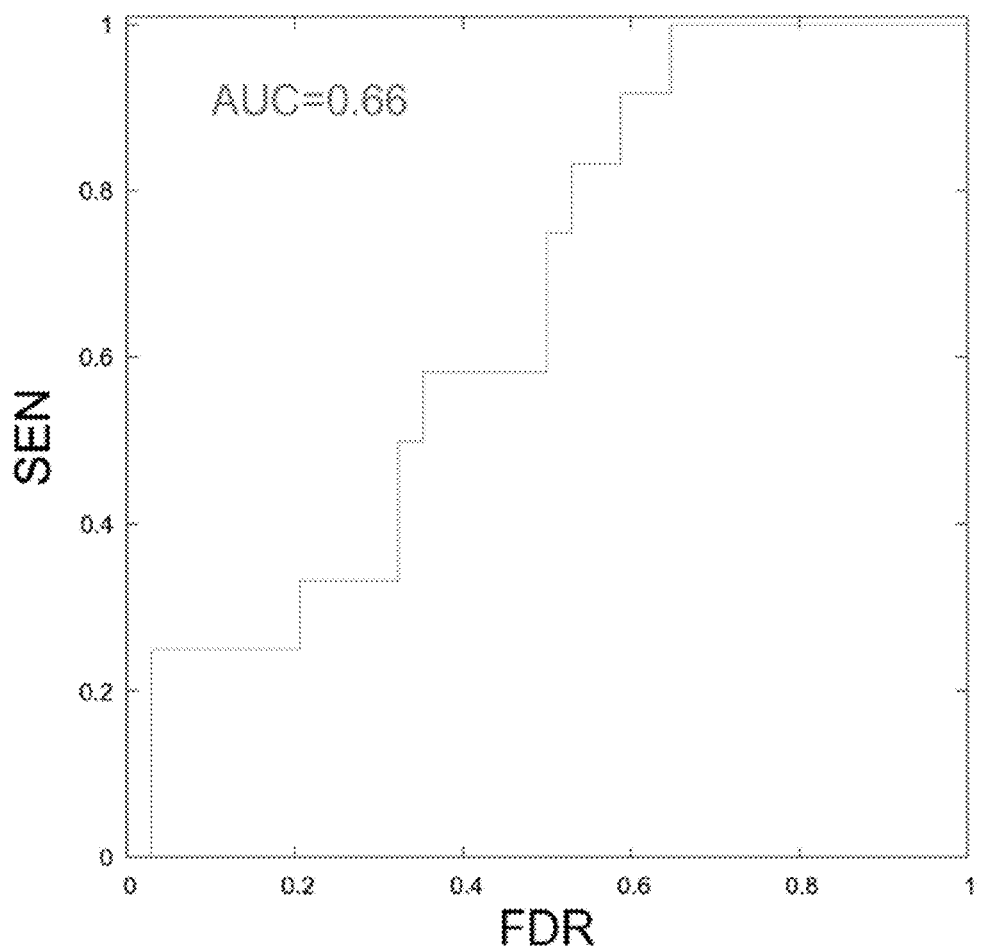
FIG. 9 illustrates a ROC curve for Polycomb-binding and non-Polycomb-binding histone peptides.

The microarray result identified 12 peptides as array-positive and 34 as array-negative with a p-value cutoff of 0.001. A peptide with a mutation matrix score equal to or more favorable than the wild-type H3 peptide was predicted to be Polycomb-binding. Among 12 true binders, 10 were predicted as binders by the mutation matrix score; among 34 true non-binders, the mutation matrix predicted 16 as non-binders, resulting in a sensitivity and accuracy of 10/12=0.833 and (10+16)/46=0.565 respectively and an area under the receiver operating curve (ROC) of 0.66. The result is satisfactory considering that no any complicated feature structure was conducted and one single score was used to discriminate binders against non-binders (FIG. 9). To further justify the prediction ability of the mutation score, its average for both binders and non-binders were also calculated. For 12 binders, the average score is −5.48 with standard deviation of 8.31; for 34 non-binders, the average score is 0.16 with standard deviation of 10.72. The p-value of the t-test between the two distributions is 0.037 using the R software package, which demonstrates a strong trend of discrimination between binder and non-binder by mutation matrix score.

IV. Combination of Simulation Data with Proteome Scan

A. Polycomb-Binding Peptides (PBP) and Proteome Scan Strategy

Based on the encouraging agreement between the predictions of the mutation matrix and the experimental data, the simulations can be used as a tool in scanning the proteome for Polycomb-binding peptides. Since there is no systematic way to identify methylated lysines in a high-throughput manner, the instant computational predictions provide a candidate list of putative methylations to serve as a starting point for experimental study.

The goal is to find peptides in the fly proteome that contain a methylated lysine residue that can be recognized by the Polycomb chromodomain. These peptides can be called as Polycomb-binding peptides (PBPs). The template peptide H3K27me3 is 9 amino acids long and has the sequence of LATKAARKS (SEQ ID NO: 88), the second lysine of which is H3K27. Thus, peptides of 9-amino-acid length with alysine on the eighth residue that show similar or better binding than that of H3 (H3K27me3) were searched for. For this purpose, a three-stage strategy was implemented to narrow down the searching space in a stepwise manner. In addition to removing peptides with a mutation score worse than the H3K27me3 peptide, filters of sequence conservation, sub-cellular location, and mass-spectrometry evidence were implemented to further reduce false positives (see below for details).

B. Proteome Scan and Filters

Figure 10:
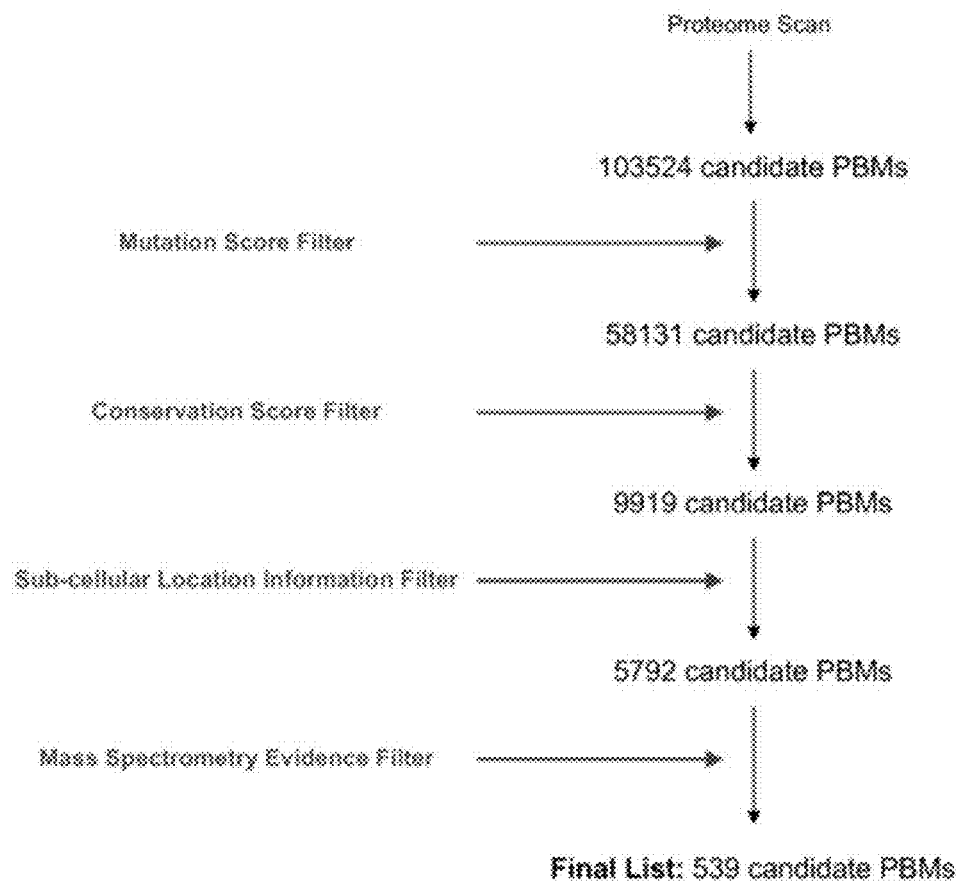
FIG. 10 illustrates a proteome scan flowchart.

Candidate PBPs in the *D. melanogaster* proteome were searched for. The overall scheme is shown in FIG. 10. 103,524 candidate peptides were first identified, each of which is a sequence of 9 amino acids for which the eighth residue is lysine. Mutation scores were calculated for all the peptides and 58,131 peptides with favorable binding energy (mutation score no higher than zero) were kept.

If a peptide binds to the Polycomb chromodomain, it is expected to be conserved through evolution since mutations may disrupt the functional interaction. It is thus reasonable to remove peptides that are not conserved at all the 9 amino acids or at the methylated lysine (the eighth) position. By considering the conservation score for the entire peptide and the lysine site, 9,919 peptides were kept for further analysis.

Since the Polycomb protein is localized in the nucleus and functions as a reader of chromatin modifications, identifying its interacting partners that are also compartmented to the nucleus was focused on. For the proteins without annotation of their sub-cellular location, they were kept as their predicted interactions with Polycomb may shed lights on their functional roles. As a result, 5,792 peptides from proteins with a sub-cellular location annotated to be either "nucleus" or "unknown" in Uniprot's general annotation[10, 11] passed this filter.

Because recognition by Polycomb protein requires the lysine residue to be methylated, the mass-spectrometry evidence of lysine-methylated peptides can provide supporting information for PBP identification. all the publicly available mass spectra were collected and a scan of the *D. melanogaster* proteome was performed to identify lysine methylation. Even though the mass spectrometry experiments were not designed to detect methyllysine, such additional evidence can help to identify the most possible binding peptides of the Polycomb chromodomain. It was found that 539 among the 5,792 peptides showed possible addition of methyl group to lysine suggested by the mass spectrometric signals PBPs V. GO Clustering Analysis To discover unknown functions of the Polycomb protein, GO clustering analysis was conducted using DAVID[12] on the 357 proteins containing the 539 filtered peptides. It was found that GO terms of "regulation of transcription" and "histone modification" are most enriched, accounting for five out of six top enriched GO clusters. Moreover, several important proteins were included in the list, such as mediator subunits 23 and 31, which involves recruitment of RNA polymerase II to promoter region that leads to start of transcription, and sex combs extra (Sce), subunit of PRC1 complex regulating gene repression in the context of methylated H3K9 and H3K27. Also, several histone-related methyltransferase, demethyltransferase, and acetyltransferase were found in the list, such as Art4, Jhd1, Kdm4B, and Tip60.

A. Chromatin Modification

Polycomb's known function is related to H3K9me3/H3K27me3 mediated gene repression by PRC1. From this analysis, it was found that Polycomb protein could also involve in gene regulation through chromatin modification with several other proteins, including histone methyltransferase, acetyltransferase, demethyltransferase and several nucleosome remodeling proteins.

ASH1, CARM1, MOF, and KDM4B are related to gene regulation by either adding histone marks or remove marks. ASH1 and CARM1 are two methyltransferases. ASH1 specifically trimethylates H3K4, an activation mark, and prevents inappropriate Polycomb silencing of important genes during development[13,14]. CARM1 methylates H3R17 and activate transcription through chromatin remodeling[15]. MOF is a probable histone acetyltransferase to H4K16 on male X chromosome to balance the gene expression between male and female[16]. KDM4B is a probable demethyltransferase that demethylates methylated H3K9 and H3K36. All these proteins are related to either adding activation marks, H3K4me3 (ASH1), H3R17me2 (CARM1), and H4K16ac (MOF), removing repression mark, H3K9me3 (KDM4B), or removing activation mark, H3K36me3 (KDM4B). All these findings indicate that Polycomb may be involved in a much more complicated gene regulation network related to chromatin modification than what we have known so far.

RING1 and CAF1, two other putative binding targets of Polycomb, are components of PRC1[17] and PRC2[18], respectively. Intriguingly, Polycomb itself is also a component of PRC1. The binding to RING1 is related to recruit Polycomb to form PRC1 complex and the binding to CAF1 is related to recruit PRC1 to PRC2.

CAF1 is also a component of chromatin assembly factor 1 (CAF-1), the nucleosome remodeling and deacetylase complex (NuRD), and the nucleosome remodeling factor (NuRF)[19-23]. IPYR, another component of NuRF[21,24], is also included in the putative binder list. These interactions suggest that Polycomb may have further function in chromatin modification related gene regulation.

B. Transcription Regulation

It was surprising to find that the potential Polycomb binders include several transcription regulation proteins. Most of these proteins are involved in the *Drosophila* development or gene transcription. Putative Polycomb binders that are functional in development include hemeotic gene (TSH)[25], eye development (SRC42 and BARH1)[26,27], neural development (SOS and PNT1)[28,29], and other development-related genes (VAV, DORS, EAF, CIC, and APTE)[30-34]. Putative Polycomb binders involving transcription include TAF[35], the largest component of the TFIID basal transcription factor complex; MED23 and MED31, components of Mediator complex and co-activators of nearly all Pol II-dependent genes; RPA2, the second largest component of RNA polymerase I; RPB2 and RPB9, components of RNA polymerase II; and RPC6, component of RNA polymerase III. Until now, little has been known about the function of the interaction of Polycomb in transcription regulation. Although Polycomb may regulate gene transcription process by binding to these important protein factors, exploration of the unrevealed realm for Polycomb and its regulatory functions are further needed.

Conclusions

The Polycomb-histone H3 complex was investigated with the use of molecular dynamics (MD). By specifying the dielectric coefficient in the calculation of the binding free energy, the relative binding affinities of Polycomb to H3K27me3, H3K27me2, H3K27me1 and unmodified H3 were able to be replicated, including the counterintuitive phenomenon of the chromodomain binding more strongly to H3K27 when monomethylated than dimethylated. Residue decomposition was performed to identify the residues in Polycomb that are most critical for binding to H3K27me3, as well as the relative contributions of the H3 residues to the binding interaction. These residues formed the basis of a mutation matrix, in which the effect of mutating any single one of these residues to other amino acids was analyzed.

With an estimate of the effect of mutating a given residue in the Polycomb-H3K27me3 complex, the *Drosophila melanogaster* proteome was scanned to find peptides containing methylated lysine that could potentially be recognized by Polycomb chromodomain, apart from histones. Coupled with additional criteria including conservation, sub-cellular localization and mass spectrometry data, a set of non-histone peptides that likely interact with the Polycomb protein mediated by chromodomain-methylysine recognition were identified. Considering the lack of proteomic approaches to determine methylated lysine, the instant approach not only provides a promising alternative to suggest candidates for follow-up investigation of the biological significance of methylation in the Polycomb partner proteins but also reveal unknown functions of the important transcriptional regulator.

As discussed herewith, computational methods were developed to identify un-modified peptides recognized by such as SH3 domain (Xu et al., Proteome-wide detection of Abl1 SH3-binding peptides by integrating computational prediction and peptide microarray. *Mol Cell Proteomics* 2012, 11, O111 010389; Hou, et al., Characterization of Domain-Peptide Interaction Interface: Prediction of SH3 Domain-Mediated Protein-Protein Interaction Network in Yeast by Generic Structure-Based Models. *J Proteome Res* 2012, 11, 2982-2995) or regulatory subunit of protein kinase A (PKA)[38]. This instant study made a significant expansion to search for methyl-lysine mediated protein-protein interactions in the proteome. More importantly, the instant approach can be readily applied to identify any PTMs and suggest their possible interacting partners, which opens a new avenue of illustrating the mechanisms of how a specific PTM regulates cellular functions.

Materials and Methods

A. Modeling Procedure

The Polycomb—H3K27me3 complex structure was obtained from the Protein Data Bank (PDB)[39]. Its PDB entry code is 1PDQ. The other methylation states were formed by manually removing methyl carbons in turn from the structure data in the PDB. The module of LEAP in the AMBER 9.0[40] software package was used to prepare the models for molecular dynamics simulation. The methylated lysine residues were not recognized by the standard residue library of LEAP, and were treated as nonstandard residues. The charges for all nonstandard residues were calculated by Gaussian03[41], using the HF/6-31G* basis set, and subsequently fitted with RESP[42]. The partial charges on all nonstandard residue atoms as calculated by Gaussian03 and RESP are listed in Table V. The nonstandard residues were all handled by Gaussian03 individually and capped[43] by ACE and NME residues so that they could be treated as complete molecules. The FF03 force field[44] was used for all atoms in the model, except for the methylated zeta nitrogens of H3K27, for which the parameters of the GAFF force field[45] were used. Each Polycomb-histone complex was placed in a rectangular, periodic box of TIP3P water molecules[46]. The dimensions of the box extended 10 Å past the solute system on all sides. When necessary, Cl⁻ counterions were added to neutralize the system for each model.

TABLE V

Partial Charges for Methylated Lysines

| Atom | Charge (Kme1) | Charge (Kme2) | Charge (Kme3) |
|---|---|---|---|
| N | −0.359144 | −0.463809 | −0.491982 |
| H | +0.227761 | +0.293639 | +0.294816 |
| C | +0.433568 | +0.573691 | +0.560647 |

TABLE V-continued

Partial Charges for Methylated Lysines

| Atom | Charge (Kme1) | Charge (Kme2) | Charge (Kme3) |
|---|---|---|---|
| O | −0.565598 | −0.513864 | −0.510015 |
| $C_\alpha$ | +0.338323 | +0.161325 | +0.201354 |
| $H_\alpha$ | +0.043801 | −0.004430 | −0.013975 |
| $C_\beta$ | −0.136320 | +0.001790 | +0.044461 |
| $H_\beta$ | +0.045217 | +0.014588 | −0.004926 |
| $C_\gamma$ | −0.106174 | −0.109808 | −0.147774 |
| $H_\gamma$ | +0.039519 | +0.030730 | +0.028426 |
| $C_\delta$ | +0.030859 | +0.168799 | +0.297319 |
| $H_\delta$ | +0.027544 | +0.009260 | −0.020336 |
| $C_\epsilon$ | −0.057268 | −0.137314 | −0.151834 |
| $H_\epsilon$ | +0.111273 | +0.095569 | +0.089085 |
| $N_\zeta$ | −0.035504 | +0.130253 | +0.263965 |
| $H_\zeta$ | +0.267532 | +0.221474 | N/A |
| Methyl C | −0.262843 | −0.200001 | −0.381536 |
| Methyl H | +0.155456 | +0.129660 | +0.179236 |

B. Molecular Dynamics Simulation

Each system was minimized in two stages; in the first stage, the water molecules and counter-ions were relaxed while organic molecules were restrained by a harmonic force of 100 kcal/mol Å². In the second stage, the restraints were released and the entire system was minimized. Each stage consisted of 400 steps of steepest descent followed by 1600 steps of conjugate gradient minimization. After the minimization stages, the systems were heated from 0 to 300 K over 30 ps. The temperature of 300 K and pressure of 1 atm were maintained by a Berendsen thermo- and barostat with a coupling time[47] of 0.2 ps. The SHAKE algorithm was used to restrain all bonds involving hydrogen.[48] Initial temperatures were assigned randomly according to the Maxwell-Boltzmann distribution at the start of the heating run. The systems were then equilibrated for 200 ps followed by production runs lasting 4 ns. During the equilibration and production runs, the heavy atoms in the Polycomb protein were restrained by a harmonic force of 10 kcal/mol Å² in order to ensure complex stability.

C. Trajectories are Most Stable at Moderate Run Length

In order to determine the optimal interval within the trajectory for calculating binding free energies, the root mean square deviation (RMSD) were calculated for the complex, the H3 peptide and the Polycomb protein over the equilibration and production runs. The coordinates of the α-carbon atoms of the residues were the data used to calculate the RMSD values. For the protein, the RMSD remained below 0.20 over the entire 4.2 ns trajectory, as expected (because of the harmonic restraints). Therefore, virtually all fluctuation in the RMSD for the complex is due to the movement of the H3 peptide which was not restrained. Since the RMSD appears to be most stable in the interval between 1.0 and 2.0 ns in the production run, this interval was chosen for binding free energy calculation analysis. In order to show that the stability of the peptide conformation is not drastically affected by a point mutation in the Polycomb protein, the RMSD of the complex was also provided for the protein mutation Y26G.

D. Determination of Optimal Dielectric Constant ∈

The calculated binding free energies for the four methylation states of H3K27 complexed with Polycomb are given in Table VI.

TABLE VI

Polycomb-H3 Complex Binding Free Energies

| Complex | Binding free energy (kcal/mol) for ∈ = 1.0 | Binding free energy (kcal/mol) for ∈ = 2.0 | Binding free energy (kcal/mol) for ∈ = 4.0 | Experimental dissociation constant (μM)² |
|---|---|---|---|---|
| Unmodified H3 | −55.27 ± 3.35 | −67.96 ± 2.79 | −74.31 ± 3.09 | >1000 |
| H3K27me1 | −59.93 ± 3.46 | −71.97 ± 2.99 | −78.00 ± 3.33 | 20 ± 3 |
| H3K27me2 | −62.71 ± 3.79 | −72.56 ± 3.28 | −77.48 ± 3.64 | 28 ± 4 |
| H3K27me3 | −69.78 ± 2.91 | −79.84 ± 2.68 | −84.87 ± 2.98 | 5 ± 1 |

Three different internal dielectric constants (1.0, 2.0 and 4.0) were supplied in the calculations. When the simulation binding free energies are graphed against the logarithms of the experimental dissociation constants (ln $K_d$), the correlation coefficients for ∈=1.0, 2.0, and 4.0 are, respectively, 0.8009, 0.9375, and 0.9851. Therefore, for this system, the binding free energies agree most closely with experiment for a dielectric constant of 4.0, including the reversal phenomenon of H3K27me2 binding more weakly to Polycomb than H3K27me1. Surprisingly, the van der Waals component of the interaction is 1.21 kcal/mol weaker for H3K27me2 than H3K27me1. This phenomenon may be due to the dimethylated cation being more energetically stable than the monomethylated one, and thus having less of a tendency to bind to the hydrophobic pocket of the chromodomain. A complete listing of the interaction components of the binding free energy for all H3K27 methylation states is given in Table VII.

TABLE VII

Binding Free Energies and Molecular Interaction Components for e = 4.0. Binding Free Energies are in kcal/mol

|  | H3K27me0 | H3K27me1 | H3K27me2 | H3K27me3 |
|---|---|---|---|---|
| GBTOT | −74.31 | −77.99 | −77.48 | −84.87 |
| GAS | −69.36 | −77.09 | −70.46 | −80.99 |
| VDW | −69.79 | −72.55 | −71.34 | −78.13 |
| ELEC | 0.43 | −4.55 | 0.88 | −2.86 |
| GBSOL | −4.95 | −0.90 | −7.02 | −3.88 |
| GBSUR | −10.57 | −10.94 | −10.86 | −11.38 |
| GB | 5.62 | 10.04 | 3.84 | 7.50 |
| GBELE | 6.05 | 5.49 | 4.72 | 4.64 |

GBTOT = binding free energy; GBTOT = GAS + GBSOL = GBELE + VDW + GBSUR
GAS = solvent-independent components of binding free energy = VDW + ELEC
VDW = van der Waals component of binding free energy
ELEC = electrostatic component of binding free energy
GBSOL = solvation-dependent components of binding free energy = GBSUR + GB
GBSUR = hydrophobic contribution to solvation free energy
GB = reaction field energy
GBELE = GB + ELEC E. Mutation Matrix Procedure The mutation matrix was formed by identifying the 21 most critical binding residues in Polycomb for binding to H3K27me3, according to Table I. Each of these residues was mutated to all of the other 19 naturally occurring amino acids. This produced 21×19=399 separate models, each a point mutation of the wild-type complex between Polycomb and histone H3. In a separate operation, the sequence of the protein was preserved and each of the H3 residues featured in the model, except for H3K27, was mutated to each of the other 19 amino acids. This produced another 8×19=152 separate models. The software program SCAP[49] was used to perform the point mutations. The standard procedure of minimization, heating and equilibration (see subsection B) was performed on each of the models, followed by 2 ns of production run. Binding free energies were calculated from the second half (the 1.0-2.0 ns interval) of the production run for each model.

F. Trajectory Analysis and Free Energy Calculation

The RMSD for each system during the equilibration and production run phases of the MD were calculated by the ptraj module in the AMBER package[40]. As a representative sample, the RMSD for the Polycomb/H3K27me3 wild-type is shown in FIG. 13. Based on the stabilization of the RMSD after about 1000 ps, the interval for the binding free energy calculation was chosen for the latter half of each production run, between 1.0 and 2.0 ns. MM-GBSA[50-52] was used to calculate the binding free energies for each Polycomb-histone complex using the mm_pbsa module in AMBER 9.0, according to the general procedure given in [8] and [53]. The binding free energies, $\Delta G_{bind}$, were calculated from 100 snapshots taken at equal intervals between the 1.0 and 2.0 ns marks of the production run trajectory. $\Delta G_{bind}$ was calculated according to:

$$\Delta G_{bind} = \langle G_{complex} \rangle - (\langle G_{protein} \rangle + \langle G_{peptide} \rangle)$$

Here, $\langle G_{complex} \rangle$, $\langle G_{protein} \rangle$ and $\langle G_{peptide} \rangle$ are the respective individual free energies of the complex, protein and peptide, and each term is calculated by summing the contributions from electrostatic potential $E_{elec}$, van der Waals potential $E_{vdw}$, and solvation free energy $G_{solv}$. In turn, $G_{solv}$ is the sum of the polar contribution $G_{polar}$ and nonpolar contribution $G_{nonpolar}$ to the solvation free energy:

$$G_{(complex/protein/peptide)} = E_{elec} + E_{vdw} + G_{solv}, G_{solv} = G_{polar} + G_{nonpolar}$$

$G_{polar}$ was calculated by setting the value of IGB to 2, activating the generalized Born parameters of Onufriev et al.[54]. $G_{nonpolar}$ was estimated to be 0.0072 times the solvent-accessible surface area (SASA), as measured by the LCPO method[55]. A grid size of 0.5 Å was used to solve the Poisson-Boltzmann equation, and the probe radius[56] was set to 1.4 Å. Three different values (1.0, 2.0, and 4.0) were used for the interior dielectric constant c in separate free energy calculations, while the external dielectric constant was given throughout as 80.0.

To investigate the molecular basis of recognition specificity, component decomposition of the binding free energy was conducted. The contributions to the binding free energy were also broken down for individual residues, and by component (van der Waals, electrostatic and solvation) for each of the complexes. Decompositions were performed by invoking the DECOMP module in the MM-GBSA program within AMBER. Each H3 or Polycomb residue was evaluated according to its overall contribution to the binding interaction.

G. Proteome Scan

The *D. melanogaster* proteome data were downloaded from Uniprot/Swissprot (2009-06-16) (The Universal Protein Resource (UniProt) in 2010. *Nucleic Acids Res* 2010, 38, D142-148; Jain et al. Infrastructure for the life sciences: design and implementation of the UniProt website. *BMC Bioinformatics* 2009, 10, 136). In total, there are 3047 protein sequences, from which all 9 amino acid long peptides containing a lysine at the eighth position from the N-terminus were extracted.

H. Mutation Score

For each candidate peptide, mutation score was calculated as:

$$\text{mutation score} = \sum_{\substack{i=1 \\ i \neq 8}}^{9} M(i, A_i),$$

where i is the amino acid position on the peptide (position 8 of the lysine was omitted), M is the mutation matrix generated from virtual mutagenesis analysis, $A_i$ is the $i^{th}$ amino acid on the candidate peptide.

I. Conservation Score

The conservation score considered the conservation of both the entire peptide and the methyllysine site. All the protein sequences in 12 fly proteomes from flybase[57] were downloaded.

For each *D. melanogaster* protein that contains a candidate peptide, its homologous proteins in the other 11 fly proteomes were found using NCBI BLAST[58]. Multiple sequence alignment was then generated for the 12 homologous proteins using CLUSTALW2[59] and the overall conservation score was calculated as:

$$\text{overall conservation score} = \sum_{\substack{i=1 \\ i \neq 8}}^{9} \sum_{m=1}^{11} \text{BLOSUM}(A_i, A_i^m),$$

where m is the index of the 11 *Drosophila* proteomes, i is the amino acid position in the candidate peptide, BLOSUM is the BLOSUM62 mutation matrix[60], $A_i$ is the $i^{th}$ amino acid in the candidate peptide, and $A_i^m$ is the $i^{th}$ amino acid in the homolog of the $m^{th}$ *Drosophila* proteome. The conservation score for the methyllysine site was defined as the number of lysine occurring at position 8 in the multiple sequence alignment. An arbitrary conservation score cutoff of 500 was used in the filtering process.

J. Mass Spectra Evidence 817,332 *D. melanogaster* mass spectra from the PRIDE database[61] were collected. All the *D. melanogaster* proteins in Uniprot/Swissprot were used as the reference database when scanning possible methyllysines by any of the three methods, X!TANDEM[62], OMSSA[63], and INSPECT[64]. For the scanning parameter, the parent mass error was set to 1 dalton, fragment mass error was set to 0.2 dalton, and modifications under consideration included mono-, di-, and trimethylation. If a lysine was identified as methylated by any of the three programs, the peptide was considered as potentially methylated to keep it in the analysis. In total, 10,838 possible methyllysines in the *D. melanogaster* proteome were found.

K. Peptide Microarray Measurement and Analysis

The chromodomain (a.a. 1-90) of Polycomb protein was expressed as GST-tagged fusion protein and purified as described in [65]. The purity of the protein was examined by SDS-PAGE electrophoresis followed by both Coomassie staining and western blot using an Anti-GST-HRP conjugate (Santa Cruz Biotechnology). The concentration of purified protein was determined by BCA assay (Amresco). A total of 46 trimethylated histone peptides were synthesized by Sigma Aldrich (desalted, mass spectrometry checked). The peptides were then printed as triplets onto glass slides (ArrayIt), together with a Cy3 marker and an anti-GST (mouse monoclonal) antibody (Thermo) as references.

The peptide microarray was rinsed with TBST buffer (25 mM Tris, 125 mM NaCl, 0.05% Tween-20, pH 8) followed by blocking with 5% non-fat milk in TBST (room temperature 1 hour or 4° C. overnight). The slide was then incubated at 4° C. with Polycomb-GST fusion protein at a final concentration of 5 mM in 5% non-fat milk/TBST for 6 hours. After washing three times for 10 minutes each with TBST, the slide was incubated with an anti-GST mouse monoclonal IgG antibody (Thermo) at a final concentration of 1 µg/mL in 5% non-fat milk/TBST and shaken gently for 1 hour at room temperature. A secondary anti-mouse IgG Dylight-488 conjugated antibody (Thermo) was added to a final concentration of 0.1 µg/mL after three more cycles of 10 minutes washing with TBST. The slide was shaken for 1 hr at room temperature and washed three times with TBST.

The dried microarray slides were scanned using a Hamamatsu NanoZoomer 2.0HT Slide Scanning System (Neuroscience Light Microscopy Facility, UCSD). Data quantification were processed using the microarray processing software ImageJ[9], where the fluorescent intensity of a microarray spot was defined as its own intensity minus the background intensity around it on the scanned image.

References

1. Paro, R. and Hogness, D. S. (1991). The Polycomb protein shares a homologous domain with a heterochromatin-associated protein of *Drosophila*. Proc. Nat. Acad. Sci. 88, 263-267.
2. Fischle, W. et al. (2003). Molecular basis for the discrimination of repressive methyl-lysine marks in histone H3 by Polycomb and HP1 chromodomains. Genes Dev. 17, 1870-1881.
3. Min, J., Zhang, Y. and Xu, R. M. (2003). Structural basis for specific binding of Polycomb chromodomain to histone H3 methylated at Lys 27. Genes Dev. 17, 1823-1828.
4. Chuikov, S. and Kurash, J. K. et al. (2004). Regulation of p53 activity through lysine methylation. Nature 432, 353-360.
5. Rathert, P. and Dhayalan, A. et al. (2008). Protein lysine methyltransferase G9a acts on non-histone targets. Nature Chem. Biol. 4, 344-346.
6. Colby, T., Matthai, A., Boeckelmann, A. and Stuible, H.-P. (2006). SUMO-Conjugating and SUMO-Deconjugating Enzymes from *Arabidopsis*. Plant Physiol. 142, 318-332.
7. Miura, K., Jin, J. B., and Hasegawa, P. M. (2007). Sumoylation, a post-translational regulatory process in plants. Cum Opin. In Plant Biol. 10, 495-502.
8. Hou, T., Chen, K., McLaughlin, W. A., Lu, B., and Wang, W. (2006). Computational analysis and prediction of the binding motif and protein interacting partners of the Abl SH3 domain. PLoSComput. Biol. 2, 0046-0055.
9. Rasband, W. S., ImageJ, US National Institutes of Health, Bethesda, Md. USA. http://rsbweb.nih.gov/ij/.
10. The Universal Protein Resource (UniProt) in 2010. Nucleic Acids Res. 38, D142-148.
11. Jain, E., Bairoch, A., Duvaud, S., Phan, I., Redaschi, N., Suzek, B. E., Martin, M. J., McGarvey, P., and Gasteiger, E. (2009). Infrastructure for the life sciences: design and implementation of the UniProt website. BMC Bioinformatics 10, 136.
12. Nature Protocols 2009; 4(1):44 & Nucleic Acids Res. 2009; 37(1):1

13. Beisel, C. et al. (2002). Histone methylation by the *Drosophila* epigenetic transcriptional regulator Ash1. Nature 419, 857-862.
14. Klymenko, T. et al. (2004). The histone methyltransferases Trithorax and Ash1 prevent transcriptional silencing by Polycomb group proteins. EMBO Rep. 5, 373-377.
15. Cakouros, D. et al. (2004). An arginine-histone methyltransferase, CARMER, coordinates ecdysone-mediated apoptosis in *Drosophila* cells. J. Biol. Chem. 279, 18467-18471.
16. Hilfiker, A. et al. (1997). M of, a putative acetyl transferase gene related to the Tip60 and MOZ human genes and to the SAS genes of yeast, is required for dosage compensation in *Drosophila*. EMBO J. 16, 2054-2060.
17. Francis, N. J. et al. (2004). Chromatin compaction by a Polycomb group protein complex. Science 306, 1574-1577.
18. Tie, F. et al. (2001). The *Drosophila* Polycomb group proteins ESC and E(Z) are present in a complex containing the histone-binding protein p55 and the histone deacetylase RPD3. Development 128, 275-286.
19. Tyler, J. K. et al. (1996). The p55 subunit of *Drosophila* chromatin assembly factor 1 is homologous to a histone deacetylase-associated protein. Mol. Cell. Biol. 16, 6149-6159.
20. Martinez-Balbas, M. A. et al. (1998). *Drosophila* NURF-55, a WD repeat protein involved in histone metabolism. PNAS 95, 132-137.
21. Gdula, D. A. et al. (1998). Inorganic pyrophosphatase is a component of the *Drosophila* nucleosome remodeling factor complex. Genes Dev. 12, 3206-3216.
22. Beall, E. L. et al. (2002). Role for a *Drosophila* Myb-containing protein complex in site-specific DNA replication. Nature 420, 833-837.
23. Taylor-Harding, B. et al. (2004). p55, the *Drosophila* ortholog of RbAp46/RbAp48, is required for the repression of dE2F2/RBF-regulated genes. Mol. Cell. Biol. 24, 9124-9136.
24. Tsukiyama, T. et al. (1995). Purification and properties of an ATP-dependent nucleosome remodeling factor. Cell 83, 1011-1020.
25. Fasano, L. et al. (1991). The gene teashirt is required for the development of *Drosophila* embryonic trunk segments and encodes a protein with widely spaced zinc finger motifs. Cell 64, 63-79.
26. Takahashi, F. et al. (1996). Regulation of cell-cell contacts in developing *Drosophila* eyes by Dsrc41, a new, close relative of vertebrate c-src. Genes Dev. 10, 1645-1656.
27. Saigo, K. et al. (1991). Identification of a different-type homeobox gene, BarH1, possibly causing Bar (B) and Om(1D) mutations in *Drosophila*. PNAS 88, 4343-4347.
28. Bonfini, L. et al. (1992). The Son of sevenless gene product: a putative activator of Ras. Science 255, 603-606.
29. Klaembt, C. et al. (1993). The *Drosophila* gene pointed encodes two ETS-like proteins which are involved in the development of the midline glial cells. Development 117, 163-176.
30. Dekel, I. et al. (2000). Identification of the *Drosophila melanogaster* homologue of the mammalian signal transducer protein, Vay. FEBS Lett. 472, 99-104.
31. Gross, I. et al. (1999). Dorsal-B, a splice variant of the *Drosophila* factor Dorsal, is a novel Rel/NF-kappaB transcriptional activator. Gene 228, 233-242.
32. Smith, E. R. et al. (2008). Regulation of the transcriptional activity of poised RNA polymerase II by the elongation factor ELL. PNAS 105, 8575-8579.
33. Goff, D. J. et al. (2001). Establishment of dorsal-ventral polarity of the *Drosophila* egg requires capicua action in ovarian follicle cells. Development 128, 4553-4562.
34. Cohen, B. et al. (1992). Apterous, a gene required for imaginal disc development in *Drosophila* encodes a member of the LIM family of developmental regulatory proteins. Genes Dev. 6, 715-729.
35. Kokubo, T. et al. (1993). *Drosophila* 230-kD TFIID subunit, a functional homolog of the human cell cycle gene product, negatively regulates DNA binding of the TATA box-binding subunit of TFIID. Genes Dev. 7, 1033-1046.
36. Xu, Z., Hou, T., Li, N., Xu, Y., and Wang, W. (2012). Proteome-wide detection of Abl1 SH3-binding peptides by integrating computational prediction and peptide microarray. Mol. Cell Proteomics 11(1): O111 010389.
37. Hou, T., Li, N., Li, Y., and Wang, W. (2012). Characterization of Domain-Peptide Interaction Interface: Prediction of SH3 Domain-Mediated Protein-Protein Interaction Network in Yeast by Generic Structure-Based Models. J. Proteome Res. 11(5): 2982-2995.
38. Hou, T., Li, Y., and Wang, W. (2011). Prediction of peptides binding to the PKA RIIalpha subunit using a hierarchical strategy. Bioinformatics 27(13): 1814-1821.
39. Berman, H. M., Westbrook, J. D., Feng, Z., Gilliand, G. L., Bhat, T. N., Weissig, H., Shindyalov, I. N. and Bourne, P. E. (2000). The Protein Data Bank. Nucleic Acids Res. 28, 235-242.
40. Case, D. A., Cheatham, T. E., Darden, T., Gohlke, H., Luo, R., Merz, K. M., Onufriev, A., Simmerling, C., Wang, B. and Woods, R. J. (2005). The Amber biomolecular simulation programs. J. Comput. Chem. 26, 1668-1688.
41. Gaussian 03, Revision C.02, M. J. Frisch and J. A. Pople et al., Gaussian Inc.
42. Bayly, C. I., Cieplak, P., Cornell, W. D. and Kollman, P. A. (1993). A well-behaved electrostatic potential based method using charge restraints for deriving atomic charges—the Resp model. J. Phys. Chem. 97, 10269-10280.
43. Cieplak, P., Cornell, W. D., Bayly, C. and Kollman, P. A. (1995). Application of the Multimolecule and Multiconformational RESP Methodology to Biopolymers: Charge Derivation for DNA, RNA, and Proteins. J. Comp. Chem. 16, 1357-1377.
44. Duan, Y., Wu, C., Chowdhury, S., Lee, M. C., Xiong, G. et al. (2003). A point-charge force field for molecular mechanics simulations of proteins. J. Comp. Chem. 24, 1999-2012.
45. Wang, J. M., Wolf, R. M., Caldwell, J. W., Kollman, P. A. and Case, D. A. (2004). Development and testing of a general amber force field. J. Comp. Chem. 25, 1157-1174.
46. Jorgensen, W. L., Chandrasekhar, J., Madura, J. D., Impey, R. W. and Klein, M. L. (1983). Comparison of simple potential functions for simulating liquid water. J. Chem. Phys. 79, 926-935.
47. Berendsen, H. J. C., Postma, J. P. M., Vangunsteren, W. F., Dinola, A. and Haak, J. R. (1984). Molecular-dynamics with coupling to an external bath. J. Chem. Phys. 81, 3684-3690.
48. Ryckaert, J., Ciccotti, G. and Berendsen, H. J. C. (1977). Numerical-integration of cartesian equations of motion of a system with constraints: Molecular-dynamics of n-alkanes. J. Comp. Phys. 23, 327-341.
49. Xiang, Z. and Honig, B. (2001). Extending the accuracy limits of prediction for side-chain conformations. J. Mol. Biol. 311, 421-430.
50. Qiu, D., Shenkin, P. S., Hollinger, F. P. and Still, W. C. (1997). The GB/SA continuum model for solvation, a fast analytical method for the calculation of approximate Born radii. *J. Phys. Chem. A* 101, 3005-3014.
51. Kollman, P. A., Massova, I., Reyes, C. M., Kuhn, B., Huo, S. et al. (2000). Calculating structures and free energies of complex molecules: combining molecular mechanics and continuum models. *Accounts of Chemical Research* 33, 889-897.
52. Wang, W., Donini, O., Reyes, C. M. and Kollman, P. A. (2001). Biomolecular simulations: recent developments in force fields, simulations of enzyme catalysis, protein-ligand, protein-protein, and protein-nucleic acid noncovalent interactions. *Annu. Rev. Biophys. Biomol. Struct.* 30, 211-243.
53. Hou, T., McLaughlin, W. A. and Wang, W. (2008). Evaluating the potency of HIV-1 protease drugs to combat resistance. *Proteins* 71, 1163-1174.
54. Onufriev, A., Bashford, D. and Case, D. A. (2000). Modification of the generalized Born model suitable for macromolecules. *J. Phys. Chem. B* 104, 3712-3720.
55. Weiser, J., Shenkin, P. S. and Still, W. C. (1999). Approximate solvent-accessible surface areas from tetrahedrally directed neighbor densities. *Biopolymers* 50, 373-380.
56. Pellegrini, E. and Field, M. J. (2002). A Generalized-Born Solvation Model for Macromolecular Hybrid-Potential Calculations. *J. Phys. Chem. A* 106, 1316-1326.
57. Tweedie, S., Ashburner, M., Falls, K., Leyland, P., McQuilton, P., Marygold, S., Millburn, G., Osumi-Sutherland, D., Schroeder, A., Seal, R. and Zhang, H. (2009). FlyBase: enhancing *Drosophila* Gene Ontology annotations. *Nucleic Acids Res.* 37, D555-559.
58. Altschul, S. F., Gish, W., Miller, W., Myers, E. W. and Lipman, D. J. (1990). Basic local alignment search tool. *J. Mol. Biol.* 215, 403-410.
59. Chenna, R., Sugawara, H., Koike, T., Lopez, R., Gibson, T. J., Higgins, D. G. and Thompson, J. D. (2003). Multiple sequence alignment with the Clustal series of programs. *Nucleic Acids Res.* 31, 3497-3500.
60. Henikoff, J. G. Amino acid substitution matrices from protein blocks. *Proc. Nat. Acad. Sci. USA* 89, 10915-10919 (1992).
61. Vizcaino, J. A., Cote, R., Reisinger, F., Foster, J. M., Mueller, M., Rameseder, J., Hermjakob, H. and Martens, L. (2009). A guide to the Proteomics Identifications Database proteomics data repository. *Proteomics* 9, 4276-4283.
62. Craig, R. and Beavis, R. C. (2004). TANDEM: matching proteins with tandem mass spectra. *Bioinformatics* 20, 1466-1467.
63. Geer, L. Y., Markey, S. P., Kowalak, J. A., Wagner, L., Xu, M., Maynard, D. M., Yang, X., Shi, W. and Bryant, S. H. (2004). Open mass spectrometry search algorithm. *J. Proteome Res.* 3, 958-964.
64. Tanner, S., Shu, H., Frank, A., Wang, L. C., Zandi, E., Mumby, M., Pevzner, P. A. and Bafna, V. (2005). InsPecT: identification of post-translationally modified peptides from tandem mass spectra. *Anal. Chem.* 77, 4626-4639.
65. Hou, T., Xu, Z., Zhang, W., McLaughlin, W. A., Case, D. A., Xu, Y., and Wang, W. (2009). Characterization of domain-peptide interaction interface: a generic structure-based model to decipher the binding specificity of SH3 domains. *Mol. Cell Proteomics* 8, 639-649.
66. Theoretical and Computation Biophysics Group, Univ. of Illinois at Urbana-Champaign.

---

The invention claimed is:

1. A method of identifying one or more binding peptides interacting with a protein of interest or a domain thereof, wherein at least one binding peptide or the protein of interest is methylated or acetylated, said method comprising:
    a) providing computational predictions for predicted unique binding peptides to the protein of interest or a domain thereof;
    b) selecting a plurality of predicted unique binding peptides based on the computational predictions;
    c) generating a peptide microarray comprising the plurality of the predicted unique binding peptides being pre-synthesized and capped with alanine at each terminus and immobilized on a solid support surface by a linker comprising aminohexanoic acid (Ahx) or polyethylene glycol (PEG), said alanine cap at each terminus stabilizing the immobilization on the solid support surface;
    d) exposing the microarray to the protein of interest or domain thereof; and
    e) detecting interactions of predicted binding peptides with the protein of interest or domain thereof on the microarray, thereby identifying one or more binding peptides interacting with a protein of interest or a domain thereof.

2. The method of claim 1, wherein said computational predictions comprises a combination of at least three analytical approaches selected from the group consisting of structural information, energetic pattern of said peptide-protein interactions, molecular dynamics simulation, conservation during evolution, mutation, subcellular location, functional filtering processes, proteome scan, and mass spectra evidence.

3. The method of claim 1, wherein between 100-1000 predicted unique binding peptides are immobilized on the solid support surface.

4. The method of claim 1, wherein the linker comprises polyethylene glycol (PEG).

5. The method of claim 1, wherein at least one predicted unique binding peptide is methylated.

6. The method of claim 1, wherein said protein of interest or a domain thereof is methylated.

7. The method of claim 1, wherein said detecting comprises detection of a fluorescent signal that correlates with a binding affinity and provides a quantitative measurement of interaction between said binding peptides and said protein of interest or protein domain thereof.

8. The method of claim 1, wherein said binding peptide-protein interaction is a transient interaction.

9. The method of claim 1, wherein said linker comprises aminohexanoic acid (Ahx).

10. The method of claim 1, wherein at least one predicted unique binding peptide is acetylated.

11. The method of claim 1, wherein said protein of interest or a domain thereof is acetylated.

* * * * *

SEQUENCE LISTING

```
<160> NUMBER OF SEQ ID NOS: 130

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Ala Pro Ser Tyr Ser Pro Pro Pro Pro Pro
1               5                   10

<210> SEQ ID NO 2
<211> LENGTH: 10
<212> TYPE: PRT
<213> ORGANISM: Homo sapiens

<400> SEQUENCE: 2

Ala Pro Ala Phe Pro Pro Pro Ser Pro Pro
1               5                   10

<210> SEQ ID NO 3
<211> LENGTH: 10
<212> TYPE: PRT
<213> ORGANISM: Homo sapiens

<400> SEQUENCE: 3

Pro Pro Ala Met Pro Ser Pro Pro Pro Pro
1               5                   10
```

```
<210> SEQ ID NO 4
<211> LENGTH: 10
<212> TYPE: PRT
<213> ORGANISM: Homo sapiens

<400> SEQUENCE: 4

Pro Pro Pro Pro Pro Val Pro Pro Pro Pro
1               5                   10

<210> SEQ ID NO 5
<211> LENGTH: 10
<212> TYPE: PRT
<213> ORGANISM: Homo sapiens

<400> SEQUENCE: 5

Thr Pro Pro Pro Pro Val Pro Pro Pro Pro
1               5                   10

<210> SEQ ID NO 6
<211> LENGTH: 10
<212> TYPE: PRT
<213> ORGANISM: Homo sapiens

<400> SEQUENCE: 6

Pro Pro Pro Leu Pro Ser Pro Pro Pro Pro
1               5                   10

<210> SEQ ID NO 7
<211> LENGTH: 10
<212> TYPE: PRT
<213> ORGANISM: Homo sapiens

<400> SEQUENCE: 7

Pro Pro Gly Tyr Pro Tyr Pro Pro Pro Pro
1               5                   10

<210> SEQ ID NO 8
<211> LENGTH: 10
<212> TYPE: PRT
<213> ORGANISM: Homo sapiens

<400> SEQUENCE: 8

Pro Pro Ala Phe Ser Pro Pro Pro Pro Pro
1               5                   10

<210> SEQ ID NO 9
<211> LENGTH: 10
<212> TYPE: PRT
<213> ORGANISM: Homo sapiens

<400> SEQUENCE: 9

Thr Pro Pro Met Pro Pro Pro Pro Pro Pro
1               5                   10

<210> SEQ ID NO 10
<211> LENGTH: 10
<212> TYPE: PRT
<213> ORGANISM: Homo sapiens

<400> SEQUENCE: 10

Gly Pro Pro Met Pro Pro Pro Pro Pro Pro
1               5                   10

<210> SEQ ID NO 11
<211> LENGTH: 10
```

```
<212> TYPE: PRT
<213> ORGANISM: Homo sapiens

<400> SEQUENCE: 11

Gly Pro Pro Pro Pro Pro Ala Pro
1               5

<210> SEQ ID NO 12
<211> LENGTH: 10
<212> TYPE: PRT
<213> ORGANISM: Homo sapiens

<400> SEQUENCE: 12

Ala Pro Thr Val Pro Pro Leu Pro Pro
1               5                   10

<210> SEQ ID NO 13
<211> LENGTH: 10
<212> TYPE: PRT
<213> ORGANISM: Homo sapiens

<400> SEQUENCE: 13

Pro Pro Ala Tyr Pro Pro Pro Val Pro
1               5                   10

<210> SEQ ID NO 14
<211> LENGTH: 10
<212> TYPE: PRT
<213> ORGANISM: Homo sapiens

<400> SEQUENCE: 14

Pro Pro Ser Leu Pro Pro Pro Pro Pro
1               5                   10

<210> SEQ ID NO 15
<211> LENGTH: 10
<212> TYPE: PRT
<213> ORGANISM: Homo sapiens

<400> SEQUENCE: 15

Leu Pro Pro Gly Pro Pro Pro Val Pro
1               5                   10

<210> SEQ ID NO 16
<211> LENGTH: 10
<212> TYPE: PRT
<213> ORGANISM: Homo sapiens

<400> SEQUENCE: 16

Pro Asn Gln Val Pro Pro Pro Pro Pro
1               5                   10

<210> SEQ ID NO 17
<211> LENGTH: 10
<212> TYPE: PRT
<213> ORGANISM: Homo sapiens

<400> SEQUENCE: 17

Pro Pro Pro Pro Pro Val Pro Pro Pro
1               5                   10

<210> SEQ ID NO 18
<211> LENGTH: 10
<212> TYPE: PRT
<213> ORGANISM: Homo sapiens
```

-continued

```
<400> SEQUENCE: 18

Cys Pro Leu Gln Pro Pro Pro Pro Pro
1               5                   10

<210> SEQ ID NO 19
<211> LENGTH: 10
<212> TYPE: PRT
<213> ORGANISM: Homo sapiens

<400> SEQUENCE: 19

Ser Pro Pro Leu Pro Pro Pro Pro Pro
1               5                   10

<210> SEQ ID NO 20
<211> LENGTH: 10
<212> TYPE: PRT
<213> ORGANISM: Homo sapiens

<400> SEQUENCE: 20

Ala Pro Pro Thr Pro Pro Pro Pro Pro
1               5                   10

<210> SEQ ID NO 21
<211> LENGTH: 10
<212> TYPE: PRT
<213> ORGANISM: Homo sapiens

<400> SEQUENCE: 21

Pro Pro Ala Val Pro Pro Pro Val Pro
1               5                   10

<210> SEQ ID NO 22
<211> LENGTH: 10
<212> TYPE: PRT
<213> ORGANISM: Homo sapiens

<400> SEQUENCE: 22

Pro Pro Asp Phe Pro Pro Pro Leu Pro
1               5                   10

<210> SEQ ID NO 23
<211> LENGTH: 10
<212> TYPE: PRT
<213> ORGANISM: Homo sapiens

<400> SEQUENCE: 23

Pro Pro Ala Gly Gly Pro Pro Pro Pro
1               5                   10

<210> SEQ ID NO 24
<211> LENGTH: 10
<212> TYPE: PRT
<213> ORGANISM: Homo sapiens

<400> SEQUENCE: 24

Pro Pro Pro Pro Pro Pro Gly Pro Pro
1               5                   10

<210> SEQ ID NO 25
<211> LENGTH: 10
<212> TYPE: PRT
<213> ORGANISM: Homo sapiens

<400> SEQUENCE: 25

Pro Val Ala Pro Pro Pro Pro Pro Pro
```

```
                   1               5                  10

<210> SEQ ID NO 26
<211> LENGTH: 10
<212> TYPE: PRT
<213> ORGANISM: Homo sapiens

<400> SEQUENCE: 26

Ala Pro Ser Gly Pro Pro Pro Pro Pro Pro
1               5                  10

<210> SEQ ID NO 27
<211> LENGTH: 10
<212> TYPE: PRT
<213> ORGANISM: Homo sapiens

<400> SEQUENCE: 27

Val Ala Pro Pro Pro Pro Pro Pro Pro Pro
1               5                  10

<210> SEQ ID NO 28
<211> LENGTH: 10
<212> TYPE: PRT
<213> ORGANISM: Homo sapiens

<400> SEQUENCE: 28

Gly Pro Val Ala Pro Pro Pro Pro Pro Pro
1               5                  10

<210> SEQ ID NO 29
<211> LENGTH: 10
<212> TYPE: PRT
<213> ORGANISM: Homo sapiens

<400> SEQUENCE: 29

Ser Arg Gly Gly Pro Pro Pro Pro Pro Pro
1               5                  10

<210> SEQ ID NO 30
<211> LENGTH: 10
<212> TYPE: PRT
<213> ORGANISM: Homo sapiens

<400> SEQUENCE: 30

Gly Pro Pro Met Pro Pro Pro Pro Pro Pro
1               5                  10

<210> SEQ ID NO 31
<211> LENGTH: 10
<212> TYPE: PRT
<213> ORGANISM: Homo sapiens

<400> SEQUENCE: 31

Gly Arg Gly Gly Pro Pro Pro Pro Pro Pro
1               5                  10

<210> SEQ ID NO 32
<211> LENGTH: 10
<212> TYPE: PRT
<213> ORGANISM: Homo sapiens

<400> SEQUENCE: 32

Leu Pro Pro Pro Pro Leu Pro Pro Pro Pro
1               5                  10
```

```
<210> SEQ ID NO 33
<211> LENGTH: 10
<212> TYPE: PRT
<213> ORGANISM: Homo sapiens

<400> SEQUENCE: 33

Pro Pro Pro Pro Pro Met Pro Pro Pro Pro
1               5                   10

<210> SEQ ID NO 34
<211> LENGTH: 10
<212> TYPE: PRT
<213> ORGANISM: Homo sapiens

<400> SEQUENCE: 34

Arg Pro Leu His Pro Pro Pro Pro Pro Pro
1               5                   10

<210> SEQ ID NO 35
<211> LENGTH: 10
<212> TYPE: PRT
<213> ORGANISM: Homo sapiens

<400> SEQUENCE: 35

Tyr Pro Pro Tyr Pro Pro Pro Pro Tyr Pro
1               5                   10

<210> SEQ ID NO 36
<211> LENGTH: 10
<212> TYPE: PRT
<213> ORGANISM: Homo sapiens

<400> SEQUENCE: 36

Pro Leu Ala Leu Pro Pro Pro Pro Pro Pro
1               5                   10

<210> SEQ ID NO 37
<211> LENGTH: 10
<212> TYPE: PRT
<213> ORGANISM: Homo sapiens

<400> SEQUENCE: 37

Pro Pro Pro Pro Pro Pro Pro Leu Pro Pro
1               5                   10

<210> SEQ ID NO 38
<211> LENGTH: 10
<212> TYPE: PRT
<213> ORGANISM: Homo sapiens

<400> SEQUENCE: 38

Pro Pro Pro Pro Pro Pro Pro Pro Leu Pro
1               5                   10

<210> SEQ ID NO 39
<211> LENGTH: 10
<212> TYPE: PRT
<213> ORGANISM: Homo sapiens

<400> SEQUENCE: 39

Leu Pro Pro Pro Pro Pro Pro Pro Pro Pro
1               5                   10

<210> SEQ ID NO 40
<211> LENGTH: 10
<212> TYPE: PRT
```

<213> ORGANISM: Homo sapiens

<400> SEQUENCE: 40

Leu Arg Ala Pro Gly Tyr Pro Ser Ser Pro
1               5                   10

<210> SEQ ID NO 41
<211> LENGTH: 10
<212> TYPE: PRT
<213> ORGANISM: Homo sapiens

<400> SEQUENCE: 41

Arg Pro Pro Pro Pro Pro Pro Pro Pro Pro
1               5                   10

<210> SEQ ID NO 42
<211> LENGTH: 10
<212> TYPE: PRT
<213> ORGANISM: Homo sapiens

<400> SEQUENCE: 42

Thr Arg Pro Pro Pro Pro Pro Pro Pro Pro
1               5                   10

<210> SEQ ID NO 43
<211> LENGTH: 10
<212> TYPE: PRT
<213> ORGANISM: Homo sapiens

<400> SEQUENCE: 43

Pro Leu Leu Pro Pro Gln Pro Ala Thr Pro
1               5                   10

<210> SEQ ID NO 44
<211> LENGTH: 10
<212> TYPE: PRT
<213> ORGANISM: Homo sapiens

<400> SEQUENCE: 44

Lys Pro Pro Pro Ala Leu Pro Pro Pro Pro
1               5                   10

<210> SEQ ID NO 45
<211> LENGTH: 10
<212> TYPE: PRT
<213> ORGANISM: Homo sapiens

<400> SEQUENCE: 45

Pro Pro Gln Gly Pro Pro Pro Pro Pro Pro
1               5                   10

<210> SEQ ID NO 46
<211> LENGTH: 10
<212> TYPE: PRT
<213> ORGANISM: Homo sapiens

<400> SEQUENCE: 46

Ala Pro Ser Pro Ala Pro Pro Pro Pro Pro
1               5                   10

<210> SEQ ID NO 47
<211> LENGTH: 10
<212> TYPE: PRT
<213> ORGANISM: Homo sapiens

<400> SEQUENCE: 47

```
Gly Pro Gly Lys Pro Pro Pro Pro Pro
1               5                   10
```

<210> SEQ ID NO 48
<211> LENGTH: 10
<212> TYPE: PRT
<213> ORGANISM: Homo sapiens

<400> SEQUENCE: 48

```
Pro Pro Pro Gln Pro Pro Pro Ala Pro
1               5                   10
```

<210> SEQ ID NO 49
<211> LENGTH: 10
<212> TYPE: PRT
<213> ORGANISM: Homo sapiens

<400> SEQUENCE: 49

```
Pro Pro Glu Tyr Pro Pro Pro Pro Pro
1               5                   10
```

<210> SEQ ID NO 50
<211> LENGTH: 10
<212> TYPE: PRT
<213> ORGANISM: Homo sapiens

<400> SEQUENCE: 50

```
Pro Met Pro Pro Pro Leu Pro Pro Pro
1               5                   10
```

<210> SEQ ID NO 51
<211> LENGTH: 10
<212> TYPE: PRT
<213> ORGANISM: Homo sapiens

<400> SEQUENCE: 51

```
Phe Pro Pro Leu Pro Pro Pro Pro Pro
1               5                   10
```

<210> SEQ ID NO 52
<211> LENGTH: 10
<212> TYPE: PRT
<213> ORGANISM: Homo sapiens

<400> SEQUENCE: 52

```
Pro Ser Ser Pro Pro Pro Pro Pro Pro
1               5                   10
```

<210> SEQ ID NO 53
<211> LENGTH: 10
<212> TYPE: PRT
<213> ORGANISM: Homo sapiens

<400> SEQUENCE: 53

```
Ser Pro Pro Ser Ser Pro Pro Pro Pro
1               5                   10
```

<210> SEQ ID NO 54
<211> LENGTH: 10
<212> TYPE: PRT
<213> ORGANISM: Homo sapiens

<400> SEQUENCE: 54

```
Cys Lys Leu Met Pro Pro Pro Pro Pro
1               5                   10
```

```
<210> SEQ ID NO 55
<211> LENGTH: 10
<212> TYPE: PRT
<213> ORGANISM: Homo sapiens

<400> SEQUENCE: 55

Pro Pro Leu Cys Pro Pro Pro Pro Pro Pro
1               5                   10

<210> SEQ ID NO 56
<211> LENGTH: 10
<212> TYPE: PRT
<213> ORGANISM: Homo sapiens

<400> SEQUENCE: 56

Pro Pro Leu Pro Ser Pro Pro Pro Pro Pro
1               5                   10

<210> SEQ ID NO 57
<211> LENGTH: 10
<212> TYPE: PRT
<213> ORGANISM: Homo sapiens

<400> SEQUENCE: 57

Pro Pro Pro Val Ser Pro Pro Pro Leu Pro
1               5                   10

<210> SEQ ID NO 58
<211> LENGTH: 10
<212> TYPE: PRT
<213> ORGANISM: Homo sapiens

<400> SEQUENCE: 58

Pro Pro Pro Leu Cys Pro Pro Pro Pro Pro
1               5                   10

<210> SEQ ID NO 59
<211> LENGTH: 10
<212> TYPE: PRT
<213> ORGANISM: Homo sapiens

<400> SEQUENCE: 59

Arg Pro Ala Pro Pro Pro Pro Pro Pro Pro
1               5                   10

<210> SEQ ID NO 60
<211> LENGTH: 10
<212> TYPE: PRT
<213> ORGANISM: Homo sapiens

<400> SEQUENCE: 60

Pro Pro Pro Leu Pro Ser Pro Pro Pro Pro
1               5                   10

<210> SEQ ID NO 61
<211> LENGTH: 9
<212> TYPE: PRT
<213> ORGANISM: Drosophila melanogaster

<400> SEQUENCE: 61

Gly Val Ile Pro His Ile His Lys Ser
1               5

<210> SEQ ID NO 62
```

```
<211> LENGTH: 9
<212> TYPE: PRT
<213> ORGANISM: Drosophila melanogaster

<400> SEQUENCE: 62

Gly Arg Ile His Arg His Leu Lys Ser
1               5

<210> SEQ ID NO 63
<211> LENGTH: 9
<212> TYPE: PRT
<213> ORGANISM: Drosophila melanogaster

<400> SEQUENCE: 63

Arg Glu Ile Arg Arg Tyr Gln Lys Ser
1               5

<210> SEQ ID NO 64
<211> LENGTH: 9
<212> TYPE: PRT
<213> ORGANISM: Drosophila melanogaster

<400> SEQUENCE: 64

Gly Gly Ala Lys Arg His Arg Lys Val
1               5

<210> SEQ ID NO 65
<211> LENGTH: 9
<212> TYPE: PRT
<213> ORGANISM: Drosophila melanogaster

<400> SEQUENCE: 65

Ile Tyr Ile Tyr Lys Val Leu Lys Gln
1               5

<210> SEQ ID NO 66
<211> LENGTH: 9
<212> TYPE: PRT
<213> ORGANISM: Drosophila melanogaster

<400> SEQUENCE: 66

Tyr Thr Glu His Ala Lys Arg Lys Thr
1               5

<210> SEQ ID NO 67
<211> LENGTH: 9
<212> TYPE: PRT
<213> ORGANISM: Drosophila melanogaster

<400> SEQUENCE: 67

Gln Ala Val Leu Leu Pro Lys Lys Thr
1               5

<210> SEQ ID NO 68
<211> LENGTH: 9
<212> TYPE: PRT
<213> ORGANISM: Drosophila melanogaster

<400> SEQUENCE: 68

Ser Arg Leu Ala His Tyr Asn Lys Arg
1               5

<210> SEQ ID NO 69
<211> LENGTH: 9
<212> TYPE: PRT
<213> ORGANISM: Drosophila melanogaster
```

```
<400> SEQUENCE: 69

Ser Thr Glu Leu Leu Ile Arg Lys Leu
1               5

<210> SEQ ID NO 70
<211> LENGTH: 9
<212> TYPE: PRT
<213> ORGANISM: Drosophila melanogaster

<400> SEQUENCE: 70

Val Thr Tyr Thr Glu His Ala Lys Arg
1               5

<210> SEQ ID NO 71
<211> LENGTH: 9
<212> TYPE: PRT
<213> ORGANISM: Drosophila melanogaster

<400> SEQUENCE: 71

Ile Gln Ala Val Leu Leu Pro Lys Lys
1               5

<210> SEQ ID NO 72
<211> LENGTH: 9
<212> TYPE: PRT
<213> ORGANISM: Drosophila melanogaster

<400> SEQUENCE: 72

Asn Leu Cys Ala Ile His Ala Lys Arg
1               5

<210> SEQ ID NO 73
<211> LENGTH: 9
<212> TYPE: PRT
<213> ORGANISM: Drosophila melanogaster

<400> SEQUENCE: 73

Leu Leu Pro Gly Glu Leu Ala Lys His
1               5

<210> SEQ ID NO 74
<211> LENGTH: 9
<212> TYPE: PRT
<213> ORGANISM: Drosophila melanogaster

<400> SEQUENCE: 74

Gly Lys Asp Ser Gly Lys Ala Lys Ala
1               5

<210> SEQ ID NO 75
<211> LENGTH: 9
<212> TYPE: PRT
<213> ORGANISM: Drosophila melanogaster

<400> SEQUENCE: 75

Glu Glu Thr Arg Gly Val Leu Lys Val
1               5

<210> SEQ ID NO 76
<211> LENGTH: 9
<212> TYPE: PRT
<213> ORGANISM: Drosophila melanogaster

<400> SEQUENCE: 76
```

Pro Arg Lys Gln Leu Ala Thr Lys Ala
1               5

<210> SEQ ID NO 77
<211> LENGTH: 9
<212> TYPE: PRT
<213> ORGANISM: Drosophila melanogaster

<400> SEQUENCE: 77

Arg Thr Lys Gln Thr Ala Arg Lys Ser
1               5

<210> SEQ ID NO 78
<211> LENGTH: 9
<212> TYPE: PRT
<213> ORGANISM: Drosophila melanogaster

<400> SEQUENCE: 78

Pro Ser Thr Gly Gly Val Lys Lys Pro
1               5

<210> SEQ ID NO 79
<211> LENGTH: 9
<212> TYPE: PRT
<213> ORGANISM: Drosophila melanogaster

<400> SEQUENCE: 79

Arg Ile His Arg Leu Leu Arg Lys Gly
1               5

<210> SEQ ID NO 80
<211> LENGTH: 9
<212> TYPE: PRT
<213> ORGANISM: Drosophila melanogaster

<400> SEQUENCE: 80

Gly Asn Ala Ala Arg Asp Asn Lys Lys
1               5

<210> SEQ ID NO 81
<211> LENGTH: 9
<212> TYPE: PRT
<213> ORGANISM: Drosophila melanogaster

<400> SEQUENCE: 81

Glu Leu Ala Gly Asn Ala Ser Lys Asp
1               5

<210> SEQ ID NO 82
<211> LENGTH: 9
<212> TYPE: PRT
<213> ORGANISM: Drosophila melanogaster

<400> SEQUENCE: 82

Thr Gly Gly Lys Ala Pro Arg Lys Gln
1               5

<210> SEQ ID NO 83
<211> LENGTH: 9
<212> TYPE: PRT
<213> ORGANISM: Drosophila melanogaster

<400> SEQUENCE: 83

Arg Asn Asp Glu Glu Leu Asn Lys Leu
1               5

```
<210> SEQ ID NO 84
<211> LENGTH: 9
<212> TYPE: PRT
<213> ORGANISM: Drosophila melanogaster

<400> SEQUENCE: 84

Arg Glu Ile Ala Gln Asp Phe Lys Thr
1               5

<210> SEQ ID NO 85
<211> LENGTH: 9
<212> TYPE: PRT
<213> ORGANISM: Drosophila melanogaster

<400> SEQUENCE: 85

Ala Ser Lys Asp Leu Lys Val Lys Arg
1               5

<210> SEQ ID NO 86
<211> LENGTH: 9
<212> TYPE: PRT
<213> ORGANISM: Drosophila melanogaster

<400> SEQUENCE: 86

Glu Gly Thr Lys Ala Val Thr Lys Tyr
1               5

<210> SEQ ID NO 87
<211> LENGTH: 9
<212> TYPE: PRT
<213> ORGANISM: Drosophila melanogaster

<400> SEQUENCE: 87

Pro Ala Thr Gly Gly Val Lys Lys Pro
1               5

<210> SEQ ID NO 88
<211> LENGTH: 9
<212> TYPE: PRT
<213> ORGANISM: Drosophila melanogaster

<400> SEQUENCE: 88

Leu Ala Thr Lys Ala Ala Arg Lys Ser
1               5

<210> SEQ ID NO 89
<211> LENGTH: 9
<212> TYPE: PRT
<213> ORGANISM: Drosophila melanogaster

<400> SEQUENCE: 89

Glu Glu Leu Asp Ser Leu Ile Lys Ala
1               5

<210> SEQ ID NO 90
<211> LENGTH: 9
<212> TYPE: PRT
<213> ORGANISM: Drosophila melanogaster

<400> SEQUENCE: 90

Leu Ala Arg Arg Gly Gly Val Lys Arg
1               5

<210> SEQ ID NO 91
<211> LENGTH: 9
```

<212> TYPE: PRT
<213> ORGANISM: Drosophila melanogaster

<400> SEQUENCE: 91

Met Asp Val Val Tyr Ala Leu Lys Arg
1               5

<210> SEQ ID NO 92
<211> LENGTH: 9
<212> TYPE: PRT
<213> ORGANISM: Drosophila melanogaster

<400> SEQUENCE: 92

Gly Leu Gly Lys Gly Gly Ala Lys Arg
1               5

<210> SEQ ID NO 93
<211> LENGTH: 9
<212> TYPE: PRT
<213> ORGANISM: Drosophila melanogaster

<400> SEQUENCE: 93

Ile His Lys Ser Leu Ile Gly Lys Lys
1               5

<210> SEQ ID NO 94
<211> LENGTH: 9
<212> TYPE: PRT
<213> ORGANISM: Drosophila melanogaster

<400> SEQUENCE: 94

Asp Ser Gly Lys Ala Lys Ala Lys Ala
1               5

<210> SEQ ID NO 95
<211> LENGTH: 9
<212> TYPE: PRT
<213> ORGANISM: Drosophila melanogaster

<400> SEQUENCE: 95

Asn Ala Ala Arg Asp Asn Lys Lys Thr
1               5

<210> SEQ ID NO 96
<211> LENGTH: 9
<212> TYPE: PRT
<213> ORGANISM: Drosophila melanogaster

<400> SEQUENCE: 96

Pro Asp Thr Gly Ile Ser Ser Lys Ala
1               5

<210> SEQ ID NO 97
<211> LENGTH: 9
<212> TYPE: PRT
<213> ORGANISM: Drosophila melanogaster

<400> SEQUENCE: 97

Ala Pro Ser Thr Gly Gly Val Lys Lys
1               5

<210> SEQ ID NO 98
<211> LENGTH: 9
<212> TYPE: PRT
<213> ORGANISM: Drosophila melanogaster

```
<400> SEQUENCE: 98

Ala Pro Ala Thr Gly Gly Val Lys Lys
1               5

<210> SEQ ID NO 99
<211> LENGTH: 9
<212> TYPE: PRT
<213> ORGANISM: Drosophila melanogaster

<400> SEQUENCE: 99

His Ala Val Ser Glu Gly Thr Lys Ala
1               5

<210> SEQ ID NO 100
<211> LENGTH: 9
<212> TYPE: PRT
<213> ORGANISM: Drosophila melanogaster

<400> SEQUENCE: 100

Asp Asn Ile Gln Gly Ile Thr Lys Pro
1               5

<210> SEQ ID NO 101
<211> LENGTH: 9
<212> TYPE: PRT
<213> ORGANISM: Drosophila melanogaster

<400> SEQUENCE: 101

Lys Arg Val Thr Ile Met Pro Lys Asp
1               5

<210> SEQ ID NO 102
<211> LENGTH: 9
<212> TYPE: PRT
<213> ORGANISM: Drosophila melanogaster

<400> SEQUENCE: 102

Lys Ala Gly Lys Asp Ser Gly Lys Ala
1               5

<210> SEQ ID NO 103
<211> LENGTH: 9
<212> TYPE: PRT
<213> ORGANISM: Drosophila melanogaster

<400> SEQUENCE: 103

Gly Asn Ala Ser Lys Asp Leu Lys Val
1               5

<210> SEQ ID NO 104
<211> LENGTH: 9
<212> TYPE: PRT
<213> ORGANISM: Drosophila melanogaster

<400> SEQUENCE: 104

Ala Arg Lys Ser Thr Gly Gly Lys Ala
1               5

<210> SEQ ID NO 105
<211> LENGTH: 9
<212> TYPE: PRT
<213> ORGANISM: Drosophila melanogaster

<400> SEQUENCE: 105

Lys Gly Gly Lys Gly Leu Gly Lys Gly
```

<210> SEQ ID NO 106
<211> LENGTH: 9
<212> TYPE: PRT
<213> ORGANISM: Drosophila melanogaster

<400> SEQUENCE: 106

Met Ala Gly Gly Lys Ala Gly Lys Asp
1               5

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 107

Xaa Ala Ala Pro Pro Trp Trp Ala Pro Pro Ile Pro Ala Ala
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 108

Xaa Ala Ala Pro Pro Ser Phe Ala Pro Pro Ala Ala Pro Ala Ala
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 109

Xaa Ala Ala Pro Pro Asp Tyr Ala Ala Pro Ala Ile Pro Ala Ala
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

```
<400> SEQUENCE: 110

Xaa Ala Ala Ala Pro Asn Tyr Pro Pro Pro Ile Pro Ala Ala
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 111

Xaa Ala Ala Leu Ala Ser Arg Pro Leu Pro Leu Leu Pro Ala Ala
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 112

Xaa Ala Ala Ile Ser Gln Arg Ala Leu Pro Pro Leu Pro Ala Ala
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 113

Xaa Ala Ala Tyr Tyr Gln Arg Pro Leu Pro Pro Leu Pro Ala Ala
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 114

Xaa Ala Ala Asp Pro Tyr Asp Ala Leu Pro Glu Thr Pro Ala Ala
1               5                   10                  15

<210> SEQ ID NO 115
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 115

Xaa Ala Ala Ala Gly Leu Ser Gln Pro Pro Ala Pro Pro Ala Ala
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 116

Xaa Ala Ala Thr Ser Gln Arg Ala Leu Glu Thr Ala Pro Ala Ala
1               5                   10                  15

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 117

Ala Ala Pro Pro Trp Trp Ala Pro Pro Ile Pro Ala Ala
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 118

Ala Ala Pro Pro Ser Phe Ala Pro Pro Ala Ala Pro Ala Ala
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 119

Ala Ala Pro Pro Asp Tyr Ala Ala Pro Ala Ile Pro Ala Ala
1               5                   10
```

```
<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 120

Ala Ala Ala Pro Asn Tyr Pro Pro Pro Ile Pro Ala Ala
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 121

Ala Ala Leu Ala Ser Arg Pro Leu Pro Leu Pro Ala Ala
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 122

Ala Ala Ile Ser Gln Arg Ala Leu Pro Pro Leu Pro Ala Ala
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 123

Ala Ala Tyr Tyr Gln Arg Pro Leu Pro Pro Leu Pro Ala Ala
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 124

Ala Ala Asp Pro Tyr Asp Ala Leu Pro Glu Thr Pro Ala Ala
1               5                   10
```

```
<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 125

Ala Ala Ala Gly Leu Ser Gln Pro Pro Ala Pro Pro Ala Ala
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term PEG

<400> SEQUENCE: 126

Ala Ala Thr Ser Gln Arg Ala Leu Glu Thr Ala Pro Ala Ala
1               5                   10

<210> SEQ ID NO 127
<211> LENGTH: 7
<212> TYPE: PRT
<213> ORGANISM: Drosophila melanogaster

<400> SEQUENCE: 127

Asp Leu Val Tyr Ala Ala Glu
1               5

<210> SEQ ID NO 128
<211> LENGTH: 6
<212> TYPE: PRT
<213> ORGANISM: Drosophila melanogaster

<400> SEQUENCE: 128

Asp Leu Val Tyr Ala Ala
1               5

<210> SEQ ID NO 129
<211> LENGTH: 4
<212> TYPE: PRT
<213> ORGANISM: Drosophila melanogaster

<400> SEQUENCE: 129

Asn Ile Leu Asp
1

<210> SEQ ID NO 130
<211> LENGTH: 7
<212> TYPE: PRT
<213> ORGANISM: Drosophila melanogaster

<400> SEQUENCE: 130

Leu Ala Thr Lys Ala Ala Arg
1               5
```